(12) United States Patent
Matsubara et al.

(10) Patent No.: US 11,198,690 B2
(45) Date of Patent: Dec. 14, 2021

(54) METHOD FOR PRODUCING (2S)-2-[(1H-PYRAZOL-1-YL)METHYL]-1,3-OXAZINANE DERIVATIVE

(71) Applicant: TAISHO PHARMACEUTICAL CO., LTD., Tokyo (JP)

(72) Inventors: Takaaki Matsubara, Tokyo (JP); Hiroki Urabe, Tokyo (JP); Ryo Suzuki, Tokyo (JP); Aya Futamura, Tokyo (JP); Ryo Kinoshita, Tokyo (JP); Nobutaka Hattori, Tokyo (JP); Hideaki Tabuse, Tokyo (JP); Koreaki Imura, Tokyo (JP); Norikazu Otake, Tokyo (JP)

(73) Assignee: TAISHO PHARMACEUTICAL CO., LTD., Tokyo (JP)

( * ) Notice: Subject to any disclaimer, the term of this patent is extended or adjusted under 35 U.S.C. 154(b) by 90 days.

(21) Appl. No.: 16/630,120

(22) PCT Filed: Jul. 11, 2018

(86) PCT No.: PCT/JP2018/026160
§ 371 (c)(1),
(2) Date: Jan. 10, 2020

(87) PCT Pub. No.: WO2019/013244
PCT Pub. Date: Jan. 17, 2019

(65) Prior Publication Data
US 2021/0147400 A1 May 20, 2021

(30) Foreign Application Priority Data

Jul. 13, 2017 (JP) .............................. JP2017-137277

(51) Int. Cl.
*C07D 413/14* (2006.01)
*C07D 265/06* (2006.01)

(52) U.S. Cl.
CPC ......... *C07D 413/14* (2013.01); *C07D 265/06* (2013.01)

(58) Field of Classification Search
CPC ............................ C07D 413/14; C07D 265/06
See application file for complete search history.

(56) References Cited

U.S. PATENT DOCUMENTS

2015/0183768 A1    7/2015    Futamura et al.

FOREIGN PATENT DOCUMENTS

| | | |
|---|---|---|
| EP | 2862860 A1 | 4/2015 |
| JP | 2015-131803 A | 7/2015 |
| WO | WO 01/94322 | 12/2001 |
| WO | WO 2013/187467 A1 | 12/2013 |
| WO | WO 2015/087853 A1 | 6/2015 |

OTHER PUBLICATIONS

Futamura; Bioorganic & Medicinal Chemistry, 2020, 28, 115489. DOI:10.1016/j.bmc.2020.115489 (Year: 2020).*

Zhu, Y., etaL, "Orexin Receptor Type-1 Couples Exclusively to Pertussis Toxin-Insensitive G-Proteins, While Orexin Receptor Type-2 Couples to Both Pertussis Toxin-Sensitive and -Insensitive G-Proteins," *J. Pharmacol. Sci.*, vol. 92, pp. 259-266 (2003).

Zeitzer, J.M., et al., "The neurobiology of hypocretins (orexins), narcolepsy and related therapeutic interventions," *Trends Pharmacol. Sci.*, vol. 27, pp. 368-374 (2006).

Marcus, J.N., et al., "Differential Expression of Orexin Receptors 1 and 2 in the Rat Brain," *J. Comp. Neurol*, vol. 435, pp. 6-25 (2001).

Trivedi, P., et al., "Distribution of orexin receptor mRNA in the rat brain," *FEBS Lett*, vol. 438, pp. 71-75 (1998).

Yamanaka, A., et al., "Orexins Activate Histaminergic Neurons via the Orexin 2 Receptor," *Biochemical and Biophysical Research Communications*, vol. 290, pp. 1237-1245 (2002).

Hagan, J.J., et al., "Orexin A activates locus coeruleus cell firing and increases arousal in the rat," *Proc. Natl. Acad. Sci. USA*, vol. 96, p. 10911-10916 (1999).

Nakamura, T., et al., "Orexin-induced hyperlocomotion and stereotypy are mediated by the dopaminergic system," *Brain Research*, vol. 873, pp. 181-187 (2000).

Smith, M.I., et al., "Evidence implicating a role for orexin-1 receptor modulation of paradoxical sleep in the rat," *Neuroscience Letters*, vol. 341, pp. 256-258 (2003).

Brisbare-Roch, C., et al., "Promotion of sleep by targeting the orexin system in rats, dogs and humans," *Nature Medicine*, vol. 13, pp. 150-155 (2007).

(Continued)

*Primary Examiner* — Daniel R Carcanague
(74) *Attorney, Agent, or Firm* — Finnegan, Henderson, Farabow, Garrett & Dunner, LLP

(57) ABSTRACT

Provided is a novel process for producing a (2S)-2-[(1H-pyrazol-1-yl)methyl]-1,3-oxazinane derivative.

More specifically, provided is a process for producing a (2S)-2-[(1H-pyrazol-1-yl)methyl]-1,3-oxazinane derivative represented by formula (1):

[Chemical Formula 1]

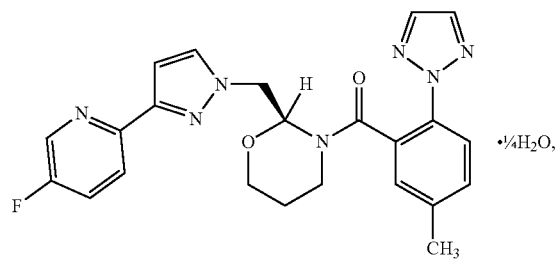

(1)

·¼H₂O, the process comprising reacting 3-aminopropan-1-ol with glyoxylic acid.

5 Claims, No Drawings

(56) References Cited

OTHER PUBLICATIONS

Cox, C.D., et al., "Discovery of the Dual Orexin Receptor Antagonist [(7R)-4-(5-Chloro-1,3-benzoxazol-2-yl)-7-methyl-1,4-diazepan-1-yl][5-methyl-2-(2H-1,2,3-triazol-2-yl)phenyl]methanone (MK-4305) for the Treatment of Insomnia," *J. Med. Chem.* vol. 53, pp. 5320-5332 (2010).
Svetlik, J., et al., "Synthesis of some Pyrazolo[1,5-c][1,3]benzoxazines and a New 5H-Pyrazolo[1,5-c][1,3,2]benzoxazaphosphorine Ring system," *J. Heterocyclic Chem.*, vol. 42, pp. 1143-1147 (2005).
Feng, L., et al., "N-Heterocyclic dicarboxylic acids: Broad-spectrum inhibitors of metallo-β-lactamases with co-antibacterial effect against antibiotic-resistant bacteria," *Bioorganic & Medicinal Chemistry Letters*, vol. 22, pp. 5185-5189 (2012).
Brands, K.M.J., et al., "Efficient Synthesis of $NK_1$ Receptor Antagonist Aprepitant Using a Crystallization-Induced Diastereoselective Transformation," *J. Am. Chem. Soc.*, vol. 125, pp. 2129-2135 (2003).
Perron-Sierra, F.M., et al., "Synthesis of a novel dioxan sialic acid analog," *Tetrahedron Letters*, vol. 45, pp. 4163-4166 (2004).
International Search Report for PCT Application No. PCT/JP2018/026160, dated Aug. 21, 2018 (two pages).
Extended European Search Report in EP App. No. 18831921.4, dated Oct. 16, 2020 (seven pages).

\* cited by examiner

METHOD FOR PRODUCING (2S)-2-[(1H-PYRAZOL-1-YL)METHYL]-1,3-OXAZINANE DERIVATIVE

This application is a national stage filing under 35 U.S.C. § 371 of International Application No. PCT/JP2018/026160, filed on Jul. 11, 2018, which claims priority of Japanese Patent Application No. JP 2017-137277, filed on Jul. 13, 2017. The contents of these applications are each incorporated herein by reference.

TECHNICAL FIELD

The present invention relates to a process for producing a (2S)-(2-{[3-(5-fluoropyridin-2-yl)-1H-pyrazol-1-yl]methyl}-1,3-oxazinan-3-yl) [5-methyl-2-(2H-1,2,3-triazol-2-yl)phenyl]methanone hydrate, which is useful as a compound having orexin (hereinafter also referred to as "OX") receptor antagonistic activity. This invention also relates to a novel intermediate compound produced during said production process.

BACKGROUND ART

Orexins are neuropeptides produced by splicing from prepro-orexin, which is specifically expressed in the lateral hypothalamus. There have been two identified neuropeptides: OX-A which consists of 33 amino acids, and OX-B which consists of 28 amino acids. These neuropeptides are both deeply involved in the regulation of sleep/wake patterns and food intake.

Both OX-A and OX-B act via OX receptors. There have been two cloned subtypes of OX receptors: OX1 and OX2 receptors, which are known as seven transmembrane, G-protein coupled receptors mainly expressed in the brain. The OX1 receptor is specifically coupled to the G-protein subclass Gq, whereas the OX2 receptor is coupled to Gq and Gi/o (see NPLs 1 and 2).

These OX receptor subtypes are different in tissue distribution—the OX1 receptor is expressed at high densities in the locus coeruleus which is the nucleus of origin of noradrenergic neurons, whereas the OX2 receptor is expressed at high densities in the tuberomammillary nucleus which is the nucleus of origin of histaminergic neurons (see NPLs 3, 4 and 5). In the raphe nucleus which is the nucleus of origin of serotoninergic neurons, and in the ventrotegmental area which is the nucleus of origin of dopaminergic neurons, expression of both OX1 and OX2 receptors has been observed (see NPL 3). Orexinergic neurons project to monoaminergic neuron systems in the brain stem and lateral hypothalamus, and have an excitatory effect on these neurons. Further, OX2 receptors are expressed in acetylcholinergic neurons in the brain stem, which are involved in the control of REM sleep, and have an influence on the activity of the nuclei of these neurons (see NPLs 3 and 4).

In recent years, there has been increased attention on the relationship of OX1 and OX2 receptors with sleep/wake regulation, and studies have been made on the usefulness of compounds having OX receptor antagonistic activity. It has been reported that intracerebroventricular administration of OX-A to rats increases locomotor activity (see NPLs 6 and 7), enhances stereotypy (see NPL 7), and prolongs arousal (see NPL 6). The REM sleep reducing effect of OX-A treatment is completely antagonized by a pretreatment with an OX receptor antagonist (see NPL 8). Further, it has been reported that administration of an orally bioavailable OX receptor antagonist capable of comparably antagonizing OX1 and OX2 receptors decreases locomotor activity, reduces sleep latency, and increases non-REM sleep and REM sleep (see NPLs 9 and 10).

There is a disclosure about a (2S)-(2-{[3-(5-fluoropyridin-2-yl)-1H-pyrazol-1-yl]methyl}-1,3-oxazinan-3-yl)[5-methyl-2-(2H-1,2,3-triazol-2-yl)phenyl]methanone hydrate, which is a compound of formula (1) having OX receptor antagonistic activity (see PTL 1).

[Chemical Formula 1]

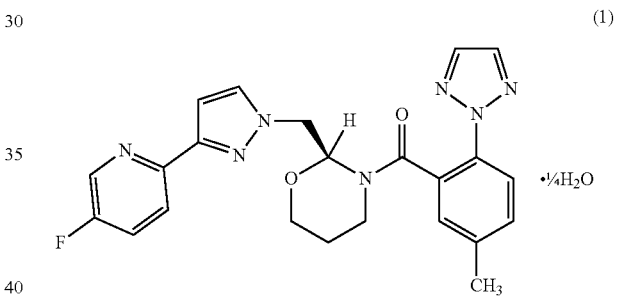

(1)

There are also disclosures about processes for synthesizing an OX1 receptor-binding compound represented by formula (1) and a synthetic intermediate thereof (see PTLs 1, 2, 3). One of those production processes for such compounds is as shown below (see PTL 3).

[Chemical Formula 2]

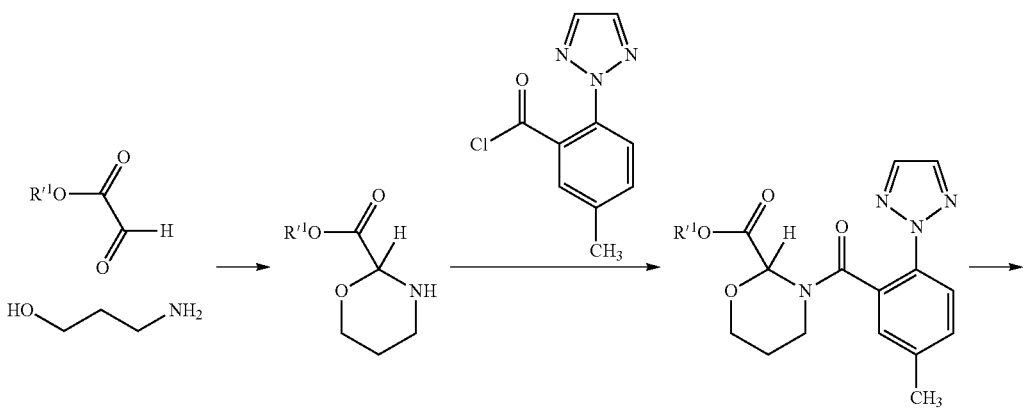

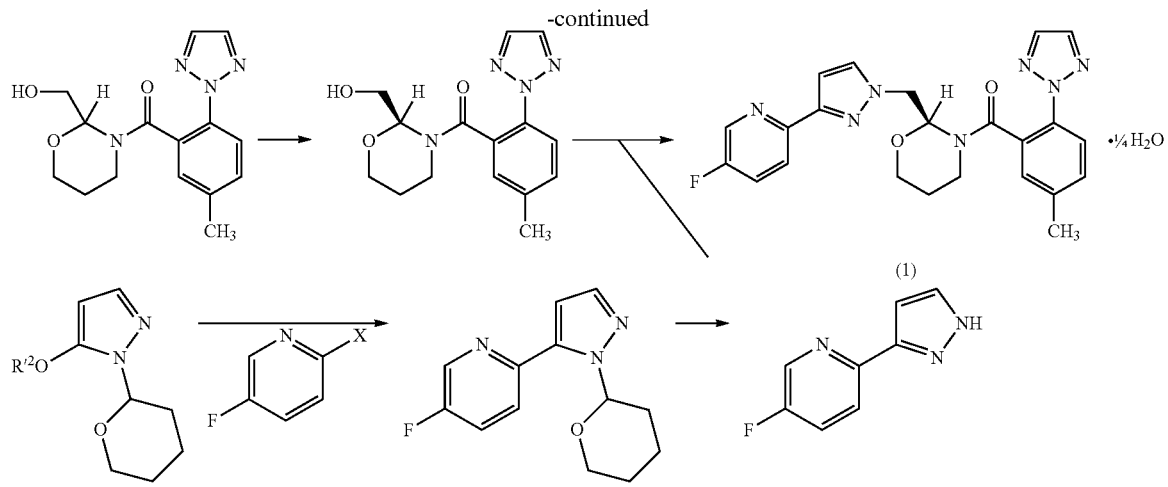

(In the above formulas, $R^{r1}$ represents a protective group for carboxylic acid; $R^{r2}$ represents a group represented by —B(OR$^{r3}$)(OR$^{r4}$) (wherein $R^{r3}$ and $R^{r4}$ may be the same or different and each represent a hydrocarbon group, and $R^{r3}$ and $R^{r4}$ may, together with the oxygen and boron atoms, form a cyclic group); and X represents a halogen atom.)

In other words, such conventional production processes for a compound of formula (1) as represented by the scheme shown above are characterized in that a 1,3-oxazinane-2-carboxylic acid ester is synthesized from a glyoxylic acid ester, and reacted with 5-methyl-2-(2H-1,2,3-triazol-2-yl)benzoyl chloride, and then the reaction product is subjected to ester reduction followed by enzymatic optical resolution, whereby a compound of formula (1) is synthesized.

However, such conventional production processes as shown above are disadvantageous in terms of production cost and are not suitable for industrial mass production due to various reasons, such as: glyoxylic acid esters are not industrially inexpensive; optical resolution is preceded by the introduction of a 5-methyl-2-(2H-1,2,3-triazol-2-yl)benzoyl moiety; and these processes involve a purification step by silica gel chromatography.

In order to solve this problem with production cost, it is required, for example, to synthesize a 1,3-oxazinane-2-carboxylic acid derivative directly from inexpensive glyoxylic acid, and to change a functional group on a nitrogen atom while maintaining the configuration at the 2-position of an optically active 1,3-oxadinane ring. However, speaking of such chemical conversion synthesis processes, the only reported process for synthesizing 1,3-oxazinane-2-carboxylic acid derivatives from glyoxylic acid is a synthesis process for polycyclic oxazinane-2-carboxylic acid derivatives, and there has been no report on a synthesis process for monocyclic oxazinane-2-carboxylic acid derivatives which easily undergo ring opening (see NPL 11). Also, no technique of changing a functional group on a nitrogen atom while maintaining the configuration at the 2-position has been reported for either of those monocyclic or polycyclic compounds.

Therefore, it may well be considered that monocyclic 1,3-oxazinane ring derivatives which are inexpensive and applicable to the synthesis of physiologically active substances having an oxazinane ring, and a conversion process for such derivatives, are generally extremely valuable.

CITATION LIST

Patent Literatures

PTL 1: International Patent Publication No. WO 2013/187467
PTL 2: International Patent Publication No. WO 2015/087853
PTL 3: Japanese Unexamined Patent Application Publication No. JP 2015-131803

Non Patent Literatures

NPL 1: Zhu Y., et al., Pharmacol. Sci., 92, 259-266, 2003.
NPL 2: Zeitzer J. M., et al., Trends Pharmacol. Sci., 27, 368-374, 2006.
NPL 3: Marcus J. N., et al., J. Comp. Neurol, 435, 6-25, 2001.
NPL 4: Trivedi J. P., et al., FEBS Lett, 438, 71-75, 1998.
NPL 5: Yamanaka A., et al., Biochem. Biophys. Res. Commun., 290, 1237-1245, 2002.
NPL 6: Hagan J. J., et al., Proc. Natl. Acad. Sci. USA, 96, 10911-10916, 1999.
NPL 7: Nakamura T., et al., Brain Res., 873, 181-187, 2000.
NPL 8: Smith M. I., et al., Neurosci. Lett., 341, 256-258, 2003.
NPL 9: Brisbare-Roch C., et al., Nat. Med., 13, 150-155, 2007.
NPL 10: Cox C. D., et al., J. Med. Chem., 53, 5320-5332, 2010.
NPL 11: Svetlik Jan, et al., J. Heterocyclic Chem., 42(6), 1143-1147, 2005.

SUMMARY OF INVENTION

Technical Problem

An object of the present invention is to provide a production process that is suitable for industrial mass production of a (2S)-(2-{[3-(5-fluoropyridin-2-yl)-1H-pyrazol-1-yl]methyl}-1,3-oxazinan-3-yl)[5-methyl-2-(2H-1,2,3-triazol-2-yl)phenyl]methanone hydrate, which is a compound of formula (1) having excellent physiological activity, through production of inexpensive intermediates of monocyclic 1,3-oxazinane-2-carboxylic acid derivatives.

Solution to Problem

The present inventors have conducted intensive studies with a view to attaining the aforementioned object, and as a result, discovered a novel process for producing compounds of formula (1), as well as novel synthetic intermediate compounds. Thus, the inventors have completed the present invention.

Also, the present inventors performed optical resolution of 1,3-oxazinane-2-carboxylic acid derivatives represented by formula (5) using appropriate chiral amines to obtain stable chiral amine salts that are applicable to industrial mass production.

Further, the inventors discovered a technique of changing a functional group on a nitrogen atom while maintaining the configuration at the 2-position of an optically active 1,3-oxazinane ring, and synthesized a (2S)-(2-{[3-(5-fluoropyridin-2-yl)-1H-pyrazol-1-yl]methyl}-1,3-oxazinan-3-yl)[5-methyl-2-(2H-1,2,3-triazol-2-yl)phenyl]methanone hydrate through conversion from (2S)-1,3-oxazinane-2-carboxylic acid represented by formula (7). Thus, the inventors have completed the present invention.

More specifically, the present invention is as defined below.

(I) A process for producing a (2S)-(2-{[3-(5-fluoropyridin-2-yl)-1H-pyrazol-1-yl]methyl}-1,3-oxazinan-3-yl)[5-methyl-2-(2H-1,2,3-triazol-2-yl)phenyl]methanone hydrate represented by formula (1):

[Chemical Formula 3]

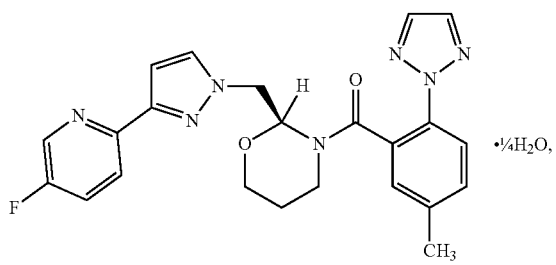

(1)

the process comprising the steps of:
(a) reacting a compound represented by formula (2):

[Chemical Formula 4]

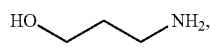

(2)

with glyoxylic acid to convert them into a compound represented by formula (3):

[Chemical Formula 5]

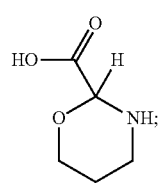

(3)

(b) condensing the compound represented by formula (3) with a compound represented by formula (4):

[Chemical Formula 6]

(4)

wherein $R^1$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-6}$ cycloalkyl group, an optionally substituted $C_{3-6}$ cycloalkenyl group, an optionally substituted $C_{1-6}$ alkoxy group, an optionally substituted $C_{2-6}$ alkenyloxy group, an optionally substituted $C_{2-6}$ alkynyloxy group, an optionally substituted $C_{3-6}$ cycloalkoxy group, an optionally substituted $C_{3-6}$ cycloalkenyloxy group, an optionally substituted aryl group, an optionally substituted heteroaryl group, a saturated or partially saturated heterocyclyl group which is optionally substituted, or an optionally substituted $C_{7-12}$ aralkyloxy group, and X represents a halogen atom, to convert them into a compound represented by formula (5):

[Chemical Formula 7]

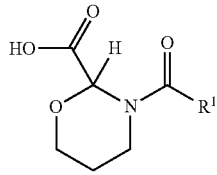

(5)

wherein $R^1$ has the same meaning as defined above;

(c) converting the compound represented by formula (5) into a compound represented by formula (6):

[Chemical Formula 8]

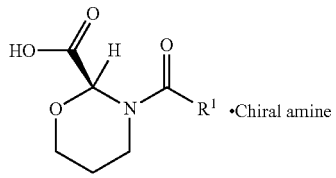

(6)

wherein $R^1$ has the same meaning as defined above, and "chiral amine" represents an optically active amine capable of forming a salt with carboxylic acid;

(d) converting the compound represented by formula (6) into a compound represented by formula (7):

[Chemical Formula 9]

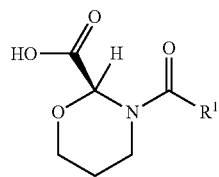

(7)

wherein R¹ has the same meaning as defined above;

(e) converting the compound represented by formula (7) into a compound represented by formula (8):

[Chemical Formula 10]

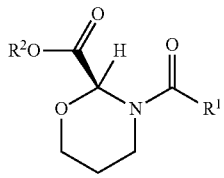

(8)

wherein R¹ has the same meaning as defined above, and R² represents a protective group for carboxylic acid;

(f) converting the compound represented by formula (8) into a compound represented by formula (9):

[Chemical Formula 11]

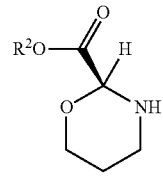

(9)

wherein R² has the same meaning as defined above;

(g) condensing the compound represented by formula (9) with a compound represented by formula (10):

[Chemical Formula 12]

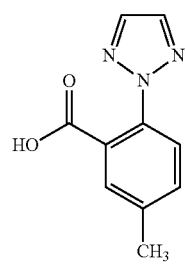

(10)

to convert them into a compound represented by formula (11):

[Chemical Formula 13]

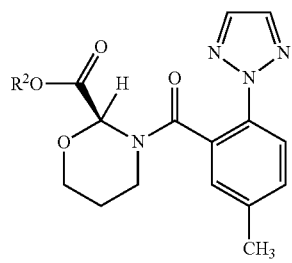

(11)

wherein R² has the same meaning as defined above;

(h) converting the compound represented by formula (11) into a compound represented by formula (12):

[Chemical Formula 14]

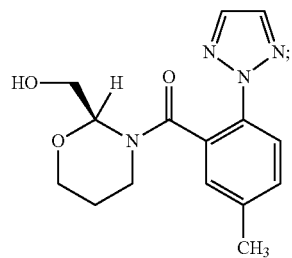

(12)

(i) reacting a compound represented by formula (13):

[Chemical Formula 15]

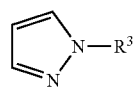

(13)

wherein R³ represents a protective group for pyrazole with a compound represented by formula (14):

[Chemical Formula 16]

(14)

wherein X has the same meaning as defined above, to convert them into a compound represented by formula (15):

[Chemical Formula 17]

(15)

wherein R³ has the same meaning as defined above;

(j) converting the compound represented by formula (15) into a compound represented by formula (16):

[Chemical Formula 18]

(16)

(k) reacting the compound represented by formula (16) with R⁴SO₂—X or (R⁴SO₂)₂O to convert them into a compound represented by formula (17):

[Chemical Formula 19]

(17)

wherein R⁴ represents an optionally substituted alkyl group, or an optionally substituted aryl group; and (l) reacting the compound represented by formula (12) with the compound represented by formula (17) to convert them into the compound represented by formula (1).

(II) A process for producing a compound represented by formula (5):

[Chemical Formula 20]

(5)

wherein R¹ has the same meaning as defined above, the process comprising the steps of:

(m) condensing the compound represented by formula (2) with the compound represented by formula (4) to convert them into a compound represented by formula (18):

[Chemical Formula 21]

(18)

wherein R¹ has the same meaning as defined above; and (n) reacting the compound represented by formula (18) with glyoxylic acid to convert them into the compound represented by formula (5).

(III) A process for producing a compound represented by formula (5):

[Chemical Formula 22]

(5)

wherein R¹ has the same meaning as defined above, the process comprising the steps of:

(o) reacting the compound represented by formula (2) with a glyoxylic acid ester to convert them into a compound represented by formula (19):

[Chemical Formula 23]

(19)

wherein $R^2$ has the same meaning as defined above;

(p) condensing the compound represented by formula (19) with the compound represented by formula (4) to convert them into a compound represented by formula (20):

[Chemical Formula 24]

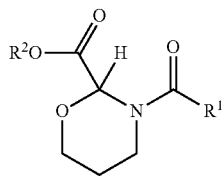

(20)

wherein $R^1$ and $R^2$ have the same meanings as defined above; and (q) converting the compound represented by formula (20) into the compound represented by formula (5).

(IV) A source material or intermediate useful for the synthesis of an optically active oxazinane ring derivative, wherein the source material or intermediate is a compound represented by formula (21):

[Chemical Formula 25]

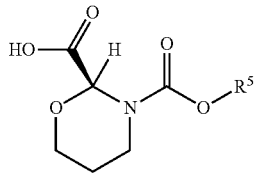

(21)

wherein $R^5$ represents an optionally substituted $C_{7-12}$ aralkyl group; or an enantiomer thereof, or a salt thereof.

(V) A compound represented by formula (22):

[Chemical Formula 26]

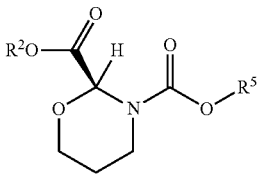

(22)

wherein $R^2$ and $R^5$ have the same meanings as defined above, or an enantiomer thereof.

Advantageous Effects of Invention

The production process of the present invention enables inexpensive synthesis of monocyclic 1,3-oxazinane-2-carboxylic acid that is applicable to the synthesis of physiologically active substances having an oxazinane ring, and allows for efficient industrial mass production of a (2S)-(2-{[3-(5-fluoropyridin-2-yl)-1H-pyrazol-1-yl]methyl}-1,3-oxazinan-3-yl)[5-methyl-2-(2H-1,2,3-triazol-2-yl)phenyl]methanone hydrate represented by formula (1).

DESCRIPTION OF EMBODIMENTS

The terms used herein shall mean as follows.

As used herein, "n" refers to normal, "i" refers to iso, "s" and "sec" refer to secondary, "t" and "tert" refer to tertiary, "c" refers to cyclo, "o" refers to ortho, "n" refers to meta, and "p" refers to para.

The "$C_{1-6}$ alkyl group" refers to a linear or branched alkyl group having 1 to 6 carbon atoms. Examples thereof include, but are not limited to, methyl group, ethyl group, n-propyl group, isopropyl group, n-butyl group, isobutyl group, sec-butyl group, tert-butyl group, n-pentyl group, isopentyl group, 2-methylbutyl group, 1-methylbutyl group, neopentyl group, 1,2-dimethylpropyl group, 1-ethylpropyl group, n-hexyl group, 4-methylpentyl group, 3-methylpentyl group, 2-methylpentyl group, 1-methylpentyl group, 3,3-dimethylbutyl group, 2,2-dimethylbutyl group, 1,1-dimethylbutyl group, 1,2-dimethylbutyl group, 1,3-dimethylbutyl group, 2,3-dimethylbutyl group, 2-ethylbutyl group, 1-ethylbutyl group, and 1-ethyl-1-methylpropyl group.

The "$C_{2-6}$ alkenyl group" refers to a linear or branched alkenyl group having 2 to 6 carbon atoms. The number of a double bond(s) present in the alkenyl group is not particularly limited. Examples of said alkenyl group include, but are not limited to, vinyl group, prop-1-en-1-yl group, allyl group, isopropenyl group, but-1-en-1-yl group, but-2-en-1-yl group, but-3-en-1-yl group, 2-methylprop-2-en-1-yl group, 1-methylprop-2-en-1-yl group, pent-1-en-1-yl group, pent-2-en-1-yl group, pent-3-en-1-yl group, pent-4-en-1-yl group, 3-methylbut-2-en-1-yl group, 3-methylbut-3-en-1-yl group, hex-1-en-1-yl group, hex-2-en-1-yl group, hex-3-en-1-yl group, hex-4-en-1-yl group, hex-5-en-1-yl group, 4-methylpent-3-en-1-yl group, and 4-methylpent-4-en-1-yl group.

The "$C_{2-6}$ alkynyl group" refers to a linear or branched alkynyl group having 2 to 6 carbon atoms. Examples thereof include, but are not limited to, ethynyl group, prop-1-yn-1-yl group, prop-2-yn-1-yl group, but-1-yn-1-yl group, but-3-yn-1-yl group, 1-methylprop-2-yn-1-yl group, pent-1-yn-1-yl group, pent-4-yn-1-yl group, hex-1-yn-1-yl group, and hex-5-yn-1-yl group.

The "$C_{3-6}$ cycloalkyl group" refers to a cyclopropyl group, a cyclobutyl group, a cyclopentyl group, or a cyclohexyl group.

The "$C_{3-6}$ cycloalkenyl group" can be exemplified, without limitation, by: 2-cyclopropen-1-yl group, 2-cyclobuten-1-yl group, 2-cyclopenten-1-yl group, 3-cyclopenten-1-yl group, 2-cyclohexen-1-yl group, 3-cyclohexen-1-yl group, 1-cyclobuten-1-yl group, and 1-cyclopenten-1-yl group.

The "$C_{1-6}$ alkoxy group" refers to a group formed by binding a $C_{1-6}$ alkyl group as defined above to an oxygen atom. Examples thereof include, but are not limited to, methoxy group, ethoxy group, n-propoxy group, isopropoxy group, n-butoxy group, isobutoxy group, sec-butoxy group, tert-butoxy group, n-pentyloxy group, isopentyloxy group, 2-methylbutoxy group, 1-methylbutoxy group, neopentyloxy group, 1,2-dimethylpropoxy group, 1-ethylpropoxy group, n-hexyloxy group, 4-methylpentyloxy group, 3-methylpentyloxy group, 2-methylpentyloxy group, 1-methylpentyloxy group, 3,3-dimethylbutoxy group, 2,2-dimethylbutoxy group, 1,1-dimethylbutoxy group, 1,2-dimethylbutoxy group, 1,3-dimethylbutoxy group, 2,3-dimethylbutoxy group, 2-ethylbutoxy group, 1-ethylbutoxy group, and 1-ethyl-1-methylpropoxy group.

The "$C_{2-6}$ alkenyloxy group" refers to a group formed by binding a $C_{2-6}$ alkenyl group as defined above to an oxygen atom. Examples thereof include, but are not limited to, vinyloxy group, and allyloxy group.

The "$C_{2-6}$ alkynyloxy group" refers to a group formed by binding a $C_{2-6}$ alkynyl group as defined above to an oxygen atom. Examples thereof include, but are not limited to, ethynyloxy group, and propargyloxy group.

The "$C_{3-6}$ cycloalkenyloxy group" refers to a group formed by binding a $C_{3-6}$ cycloalkenyl group as defined above to an oxygen atom. Examples thereof include, but are not limited to, cyclopropenyl group, cyclobutenyl group, cyclopentenyl group, and cyclohexenyl group.

The "aryl group" refers to a monocyclic or condensed polycyclic aromatic hydrocarbon group. Examples thereof include, but are not limited to, phenyl group, 1-naphthyl group, 2-naphthyl group, anthranyl group, and phenanthryl group.

The "heteroaryl group" refers to a monocyclic or condensed polycyclic aromatic heterocyclic group. The number of a ring-constituting heteroatom(s) is not particularly limited, and is from one to several, preferably approximately from 1 to 5. When two or more ring-constituting heteroatoms are present, these heteroatoms may be the same or different. Examples of heteroatoms include, but are not limited to, oxygen atom, nitrogen atom, and sulfur atom. Examples of a monocyclic heteroaryl group include, but are not limited to, various 5- to 7-membered monocyclic heteroaryl groups, such as 2-furyl group, 3-furyl group, 2-thienyl group, 3-thienyl group, 1-pyrrolyl group, 2-pyrrolyl group, 3-pyrrolyl group, 2-oxazolyl group, 4-oxazolyl group, 5-oxazolyl group, 3-isoxazolyl group, 4-isoxazolyl group, 5-isoxazolyl group, 2-thiazolyl group, 4-thiazolyl group, 5-thiazolyl group, 3-isothiazolyl group, 4-isothiazolyl group, 5-isothiazolyl group, 1-imidazolyl group, 2-imidazolyl group, 4-imidazolyl group, 5-imidazolyl group, 1-pyrazolyl group, 3-pyrazolyl group, 4-pyrazolyl group, 5-pyrazolyl group, (1,2,3-oxadiazol)-4-yl group, (1,2,3-oxadiazol)-5-yl group, (1,2,4-oxadiazol)-3-yl group, (1,2,4-oxadiazol)-5-yl group, (1,2,5-oxadiazol)-3-yl group, (1,2,5-oxadiazol)-4-yl group, (1,3,4-oxadiazol)-2-yl group, (1,3,4-oxadiazol)-5-yl group, furazanyl group, (1,2,3-thiadiazol)-4-yl group, (1,2,3-thiadiazol)-5-yl group, (1,2,4-thiadiazol)-3-yl group, (1,2,4-thiadiazol)-5-yl group, (1,2,5-thiadiazol)-3-yl group, (1,2,5-thiadiazol)-4-yl group, (1,3,4-thiadiazol)-2-yl group, (1,3,4-thiadiazol)-5-yl group, (1H-1,2,3-triazol)-1-yl group, (1H-1,2,3-triazol)-4-yl group, (1H-1,2,3-triazol)-5-yl group, (2H-1,2,3-triazol)-2-yl group, (2H-1,2,3-triazol)-4-yl group, (1H-1,2,4-triazol)-1-yl group, (1H-1,2,4-triazol)-3-yl group, (1H-1,2,4-triazol)-5-yl group, (4H-1,2,4-triazol)-3-yl group, (4H-1,2,4-triazol)-4-yl group, (1H-tetrazol)-1-yl group, (1H-tetrazol)-5-yl group, (2H-tetrazol)-2-yl group, (2H-tetrazol)-5-yl group, 2-pyridyl group, 3-pyridyl group, 4-pyridyl group, 3-pyridazinyl group, 4-pyridazinyl group, 2-pyrimidinyl group, 4-pyrimidinyl group, 5-pyrimidinyl group, 2-pyrazinyl group, (1,2,3-triazin)-4-yl group, (1,2,3-triazin)-5-yl group, (1,2,4-triazin)-3-yl group, (1,2,4-triazin)-5-yl group, (1,2,4-triazin)-6-yl group, (1,3,5-triazin)-2-yl group, 1-azepinyl group, 2-azepinyl group, 3-azepinyl group, 4-azepinyl group, (1,4-oxazepin)-2-yl group, (1,4-oxazepin)-3-yl group, (1,4-oxazepin)-5-yl group, (1,4-oxazepin)-6-yl group, (1,4-oxazepin)-7-yl group, (1,4-thiazepin)-2-yl group, (1,4-thiazepin)-3-yl group, (1,4-thiazepin)-5-yl group, (1,4-thiazepin)-6-yl group, and (1,4-thiazepin)-7-yl group.

Examples of a condensed polycyclic heteroaryl group include, but are not limited to, various 8- to 14-membered condensed polycyclic heteroaryl groups, such as 2-benzofuranyl group, 3-benzofuranyl group, 4-benzofuranyl group, 5-benzofuranyl group, 6-benzofuranyl group, 7-benzofuranyl group, 1-isobenzofuranyl group, 4-isobenzofuranyl group, 5-isobenzofuranyl group, 2-benzo[b]thienyl group, 3-benzo[b]thienyl group, 4-benzo[b]thienyl group, 5-benzo[b]thienyl group, 6-benzo[b]thienyl group, 7-benzo[b]thienyl group, 1-benzo[c]thienyl group, 4-benzo[c]thienyl group, 5-benzo[c]thienyl group, 1-indolyl group, 2-indolyl group, 3-indolyl group, 4-indolyl group, 5-indolyl group, 6-indolyl group, 7-indolyl group, (2H-isoindol)-1-yl group, (2H-isoindol)-2-yl group, (2H-isoindol)-4-yl group, (2H-isoindol)-5-yl group, (1H-indazol)-1-yl group, (1H-indazol)-3-yl group, (1H-indazol)-4-yl group, (1H-indazol)-5-yl group, (1H-indazol)-6-yl group, (1H-indazol)-7-yl group, (2H-indazol)-2-yl group, (2H-indazol)-3-yl group, (2H-indazol)-4-yl group, (2H-indazol)-5-yl group, (2H-indazol)-6-yl group, (2H-indazol)-7-yl group, 2-benzoxazolyl group, 4-benzoxazolyl group, 5-benzoxazolyl group, 6-benzoxazolyl group, 7-benzoxazolyl group, (1,2-benzisoxazol)-3-yl group, (1,2-benzisoxazol)-4-yl group, (1,2-benzisoxazol)-5-yl group, (1,2-benzisoxazol)-6-yl group, (1,2-benzisoxazol)-7-yl group, (2,1-benzisoxazol)-3-yl group, (2,1-benzisoxazol)-4-yl group, (2,1-benzisoxazol)-5-yl group, (2,1-benzisoxazol)-6-yl group, (2,1-benzisoxazol)-7-yl group, 2-benzothiazolyl group, 4-benzothiazolyl group, 5-benzothiazolyl group, 6-benzothiazolyl group, 7-benzothiazolyl group, (1,2-benzisothiazol)-3-yl group, (1,2-benzisothiazol)-4-yl group, (1,2-benzisothiazol)-5-yl group, (1,2-benzisothiazol)-6-yl group, (1,2-benzisothiazol)-7-yl group, (2,1-benzisothiazol)-3-yl group, (2,1-benzisothiazol)-4-yl group, (2,1-benzisothiazol)-5-yl group, (2,1-benzisothiazol)-6-yl group, (2,1-benzisothiazol)-7-yl group, (1,2,3-benzoxadiazol)-4-yl group, (1,2,3-benzoxadiazol)-5-yl group, (1,2,3-benzoxadiazol)-6-yl group, (1,2,3-benzoxadiazol)-7-yl group, (2,1,3-benzoxadiazol)-4-yl group, (2,1,3-benzoxadiazol)-5-yl group, (1,2,3-benzothiadiazol)-4-yl group, (1,2,3-benzothiadiazol)-5-yl group, (1,2,3-benzothiadiazol)-6-yl group, (1,2,3-benzothiadiazol)-7-yl group, (2,1,3-benzothiadiazol)-4-yl group, (2,1,3-benzothiadiazol)-5-yl group, (1H-benzotriazol)-1-yl group, (1H-benzotriazol)-4-yl group, (1H-benzotriazol)-5-yl group, (1H-benzotriazol)-6-yl group, (1H-benzotriazol)-7-yl group, (2H-benzotriazol)-2-yl group, (2H-benzotriazol)-4-yl group, (2H-benzotriazol)-5-yl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 3-cinnolinyl group, 4-cinnolinyl group, 5-cinnolinyl group, 6-cinnolinyl group, 7-cinnolinyl group, 8-cinnolinyl group, 2-quinazolinyl group, 4-quinazolinyl group, 5-quinazolinyl group, 6-quinazolinyl group, 7-quinazolinyl group, 8-quinazolinyl group, 2-quinoxalinyl group, 5-quinoxalinyl group, 6-quinoxalinyl group, 1-phthalazinyl group, 5-phthalazinyl group, 6-phthalazinyl group, 2-purinyl group, 6-purinyl group, 8-purinyl group, 9-purinyl group, 2-pteridinyl group, 4-pteridinyl group, 6-pteridinyl group, 7-pteridinyl group, 1-carbazolyl group, 2-carbazolyl group, 3-carbazolyl group, 4-carbazolyl group, 9-carbazolyl group, 2-(α-carbolinyl) group, 3-(α-carbolinyl) group, 4-(α-carbolinyl) group, 5-(α-carbolinyl) group, 6-(α-carbolinyl) group, 7-(α-carbolinyl) group, 8-(α-carbolinyl) group, 9-(α-carbolinyl) group, 1-(β-carbolinyl) group, 3-(β-carbolinyl) group, 4-(β-carbolinyl) group, 5-(β-carbolinyl) group, 6-(β-carbolinyl) group, 7-(β-carbolinyl) group, 8-(β-carbolinyl) group, 9-(β-carbolinyl) group, 1-(γ-carbolinyl) group, 2-(γ-carbolinyl) group, 4-(γ-carbolinyl) group, 5-(γ-carbolinyl) group, 6-(γ-carbolinyl) group, 7-(γ-carbolinyl) group, 8-(γ- carbolinyl) group, 9-(γ-carbolinyl) group, 1-acridinyl group, 2-acridinyl group, 3-acridinyl group, 4-acridinyl group, 9-acridinyl group, 1-phenoxazinyl group, 2-phenoxazinyl group, 3-phenoxazinyl group, 4-phenoxazinyl group, 10-phenoxazinyl group, 1-phenothiazinyl group, 2-phenothiazinyl group, 3-phenothiazinyl group, 4-phenothiazinyl group, 10-phenothiazinyl group, 1-phenazinyl group, 2-phenazinyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-thianthrenyl group, 2-thianthrenyl group, 1-indolizinyl group, 2-indolizinyl group, 3-indolizinyl group, 5-indolizinyl group, 6-indolizinyl group, 7-indolizinyl group, 8-indolizinyl group, 1-phenoxathiinyl group, 2-phenoxathiinyl group, 3-phenoxathiinyl group, and 4-phenoxathiinyl group.

The "saturated or partially saturated heterocyclyl group" refers to a saturated or partially saturated heterocyclyl group having one or more nitrogen, oxygen or sulfur atoms in the ring. Examples thereof include, but are not limited to, oxetan-3-yl group, azetidin-1-yl group, 1-pyrrolidinyl group, piperidino group, 2-piperidyl group, 3-piperidyl group, 1-piperazinyl group, morpholin-4-yl group, morpholin-3-yl group, thiomorpholin-4-yl group, thiomorpholin-3-yl group, azepan-1-yl group, 1,4-oxazepan-4-yl group, and azocan-1-yl group.

The "$C_{7-12}$ aralkyl group" refers to a group having 7 to 12 carbon atoms, in which an alkyl group as defined above is substituted with an aryl group as defined above. Examples thereof include, but are not limited to, benzyl group, 1-naphthylmethyl group, 2-naphthylmethyl group, and 1-phenethyl group.

The "$C_{7-12}$ aralkyloxy group" refers to a group formed by binding a $C_{7-12}$ aralkyl group as defined above to an oxygen atom. Examples thereof include, but are not limited to, benzyloxy group, 1-naphthylmethoxy group, 2-naphthylmethoxy group, and 1-phenethyloxy group.

The "halogen atom" refers to a fluorine atom, a chlorine atom, a bromine atom, or an iodine atom.

The "protective group for carboxylic acid" can be any group that is capable of forming a carboxylic acid ester. Examples thereof include, but are not limited to, an optionally substituted aryl group, an optionally substituted $C_{7-12}$ aralkyl group, and an optionally substituted $C_{1-6}$ alkyl group.

The "protective group for pyrazole" can be exemplified, without limitation, by: an optionally substituted $C_{1-6}$ alkylsulfonyl group, an optionally substituted $C_{1-6}$ alkylsulfonylamide, an optionally substituted $C_{1-6}$ alkylcarbamate group, an optionally substituted $C_{1-6}$ alkyl group, an optionally substituted aryl group, an optionally substituted $C_{7-12}$ aralkyl group, an optionally substituted aminoacetal group, and an optionally substituted amide.

The "aminoacetal group" can be exemplified, without limitation, by: N-hydroxymethyl group, N-methoxymethyl group, N-diethoxymethyl group, N-(2-chloroethoxy)methyl group, N-[2-(trimethylsilyl)ethoxy]methyl group, N-t-butoxymethyl group, N-t-butyldimethylsiloxymethyl group, N-pivaloyloxymethyl group, N-benzyloxymethyl group, N-4-methoxybenzyloxymethyl group, N-[1-(6-nitro-1,3-benzodioxy-5-yl)ethoxy]methyl group, N-dimethylaminomethyl group, N-acetylaminomethyl group, N-2-tetrahydropyranyl group, and N-2-tetrahydrofuranyl group.

The "amide" can be exemplified, without limitation, by: formamide, N',N'-diethylureide, dichloroacetamide, pivalamide, and t-butoxycarbonyl-N-methyl-4-aminobutanamide.

When a certain functional group is defined herein as "optionally substituted", it is meant that the functional group may have one or two or more substituents at a chemically substitutable position(s) thereof. The type(s), number, and substitution position(s) of a substituent(s) present in a functional group are not particularly limited. When two or more substituents are present, these substituents may be the same or different. Examples of substituents that can be found in a functional group include, but are not limited to, halogen atom, oxo group, thioxo group, nitro group, nitroso group, cyano group, isocyano group, cyanato group, thiocyanato group, isocyanato group, isothiocyanato group, hydroxy group, sulfanyl group, carboxy group, sulfanylcarbonyl group, oxalo group, mesoxalo group, thiocarboxy group, dithiocarboxy group, carbamoyl group, thiocarbamoyl group, sulfo group, sulfamoyl group, sulfino group, sulfinamoyl group, sulfeno group, sulfenamoyl group, phosphono group, hydroxyphosphonyl group, $C_{1-6}$ alkyl group, $C_{2-6}$ alkenyl group, $C_{2-6}$ alkynyl group, $C_{1-6}$ alkylidene group, aryl group, $C_{7-12}$ aralkyl group, $C_{7-12}$ aralkylidene group, $C_{1-6}$ alkoxy group, aryloxy group, $C_{7-12}$ aralkyloxy group, $C_{1-6}$ alkylsulfanyl group, arylsulfanyl group, $C_{7-12}$ aralkyloxysulfanyl group, $C_{1-6}$ alkanoyl group, arylcarbonyl group, $C_{1-6}$ alkylsulfonyl group, arylsulfonyl group, $C_{1-6}$ alkoxycarbonyl group, amino group, hydrazino group, hydrazono group, diazenyl group, ureido group, thioureido group, guanidino group, carbamimidoyl group (amizino group), azido group, imino group, hydroxyamino group, hydroxyimino group, aminooxy group, diazo group, semicarbazino group, semicarbazono group, allophanyl group, hydantoyl group, phosphano group, phosphoroso group, phospho group, boryl group, silyl group, oxido group, heteroaryl group, and saturated or partially saturated heterocyclyl group.

Those above-listed substituents may be further substituted with one or two or more other substituents. Examples of such further substituted substituents include, but are not limited to, $C_{1-6}$ alkyl halide group, $C_{1-6}$ alkoxy halide group, carboxy-substituted $C_{1-6}$ alkyl group, and $C_{1-6}$ alkyl-substituted amino group.

The "chiral amine" can be exemplified, without limitation, by optically active amines having an asymmetric center at the α-position of the amino group, such as (R)-phenylethylamine, (R)-1-(p-tolyl)ethylamine, (R)-1-(4-methoxyphenyl)-ethylamine, (R)-1-(4-chlorophenyl)-ethylamine, (S)-3,3-dimethyl-2-butylamine, (1S,2R)-2-amino-1-phenyl-1,3-propanediol, L-phenylalaninol, (R)-phenylglycinol, (R)-2-amino-1-propanol, and cinchonidine.

Examples of a salt of a compound represented by formula (21) include not only salts of said compound with a "chiral amine" as defined above, but also salts of said compound with one or more metal ions such as lithium ion, sodium ion, potassium ion, calcium ion, magnesium ion, zinc ion, or aluminum ion, as well as salts of said compound with an amine such as ammonia, arginine, lysine, piperazine, choline, diethylamine, 4-phenylcyclohexylamine, 2-aminoethanol, or benzathine.

Examples of a salt of an enantiomer of a compound of formula (21) include salts of said enantiomer with one or more metal ions such as lithium ion, sodium ion, potassium ion, calcium ion, magnesium ion, zinc ion, or aluminum ion, and salts of said enantiomer with an amine such as ammonia, arginine, lysine, piperazine, choline, diethylamine, 4-phenylcyclohexylamine, 2-aminoethanol, or benzathine.

The following makes reference to some preferred modes of the present invention.

In the compounds referred to in the present specification, $R^1$ is preferably an optionally substituted $C_{2-6}$ alkenyloxy group or an optionally substituted $C_{7-12}$ aralkyloxy group, more preferably an allyloxy group or a benzyloxy group.

In the compounds, $R^2$ is preferably an optionally substituted $C_{1-6}$ alkyl group, more preferably a methyl group, an ethyl group, or an isopropyl group.

In the compounds, $R^3$ is preferably an optionally substituted $C_{1-6}$ alkylsulfonylamide group, an optionally substituted $C_{1-6}$ alkoxycarbonyl group, an optionally substituted $C_{1-6}$ alkyl group, an optionally substituted aryl group, an optionally substituted $C_{7-12}$ aralkyl group, or an optionally substituted aminoacetal group, more preferably an optionally substituted aminoacetal group, particularly preferably a tetrahydropyranyl group.

In the compounds, $R^4$ is preferably an optionally substituted $C_{1-6}$ alkyl group or an optionally substituted aryl group, more preferably an optionally substituted $C_{1-6}$ alkyl group.

In the compounds, $R^5$ is preferably an optionally substituted $C_{7-12}$ aralkyl group, more preferably a benzyl group or a 1-phenethyl group.

In the compounds, X is preferably a chlorine atom or a bromine atom, more preferably a chlorine atom.

In the compounds, the chiral amine is preferably an optically active amine having an asymmetric center at the α-position of the amino group, more preferably (1S,2R)-2-amino-1-phenyl-1,3-propanediol, L-phenylalaninol, (R)-phenylglycinol, or (R)-2-amino-1-propanol.

In one of preferred modes,
$R^1$ is an optionally substituted $C_{2-6}$ alkenyloxy group, or an optionally substituted $C_{7-12}$ aralkyloxy group;
$R^2$ is an optionally substituted $C_{1-6}$ alkyl group;
$R^3$ is an optionally substituted $C_{1-6}$ alkylsulfonylamide group, an optionally substituted $C_{1-6}$ alkoxycarbonyl group, an optionally substituted $C_{1-6}$ alkyl group, an optionally substituted aryl group, an optionally substituted $C_{7-12}$ aralkyl group, or an optionally substituted aminoacetal group;
$R^4$ is an optionally substituted $C_{1-6}$ alkyl group, or an optionally substituted aryl group; and
the chiral amine is an optically active amine having an asymmetric center at the α-position of the amino group.

In another preferred mode,
$R^1$ is an allyloxy group or a benzyloxy group;
$R^2$ is an optionally substituted $C_{1-6}$ alkyl group;
$R^3$ is an optionally substituted $C_{1-6}$ alkylsulfonylamide group, an optionally substituted $C_{1-6}$ alkoxycarbonyl group, an optionally substituted $C_{1-6}$ alkyl group, an optionally substituted aryl group, an optionally substituted $C_{7-12}$ aralkyl group, or an optionally substituted aminoacetal group;
$R^4$ is an optionally substituted $C_{1-6}$ alkyl group, or an optionally substituted aryl group; and
the chiral amine is (1S,2R)-2-amino-1-phenyl-1,3-propanediol, L-phenylalaninol, (R)-phenylglycinol, or (R)-2-amino-1-propanol.

In another preferred mode,
$R^1$ is an allyloxy group or a benzyloxy group;
$R^2$ is an optionally substituted $C_{1-6}$ alkyl group;
$R^3$ is an optionally substituted aminoacetal group;
$R^4$ is an optionally substituted $C_{1-6}$ alkyl group, or an optionally substituted aryl group; and
the chiral amine is (1S,2R)-2-amino-1-phenyl-1,3-propanediol, L-phenylalaninol, (R)-phenylglycinol, or (R)-2-amino-1-propanol.

In another preferred mode,
$R^1$ is a benzyloxy group;
$R^2$ is an optionally substituted $C_{1-6}$ alkyl group;
$R^3$ is an optionally substituted aminoacetal group;
$R^4$ is an optionally substituted $C_{1-6}$ alkyl group, or an optionally substituted aryl group; and
the chiral amine is (R)-phenylglycinol.

In another preferred mode,
$R^1$ is a benzyloxy group;
$R^2$ is a methyl group, an ethyl group, or an isopropyl group;
$R^3$ is a tetrahydropyranyl group;
$R^4$ is an optionally substituted $C_{1-6}$ alkyl group; and
the chiral amine is (R)-phenylglycinol.

The present invention is directed to a process for producing the compound represented by formula (1). This invention is also directed to compounds represented by formulas (3), (5), (6), (7), (8), (9), (11), (12), (15), (16) and (17), which are production intermediates of the compound of formula (1).

The present invention can be carried out by following the procedures described below. One embodiment of this invention is illustrated in Scheme 1.

Scheme 1

[Chemical Formula 27]

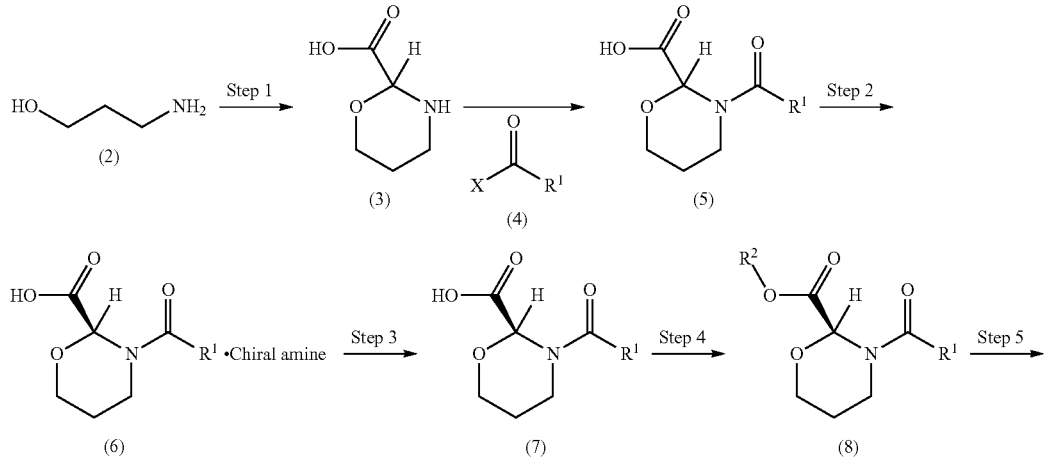

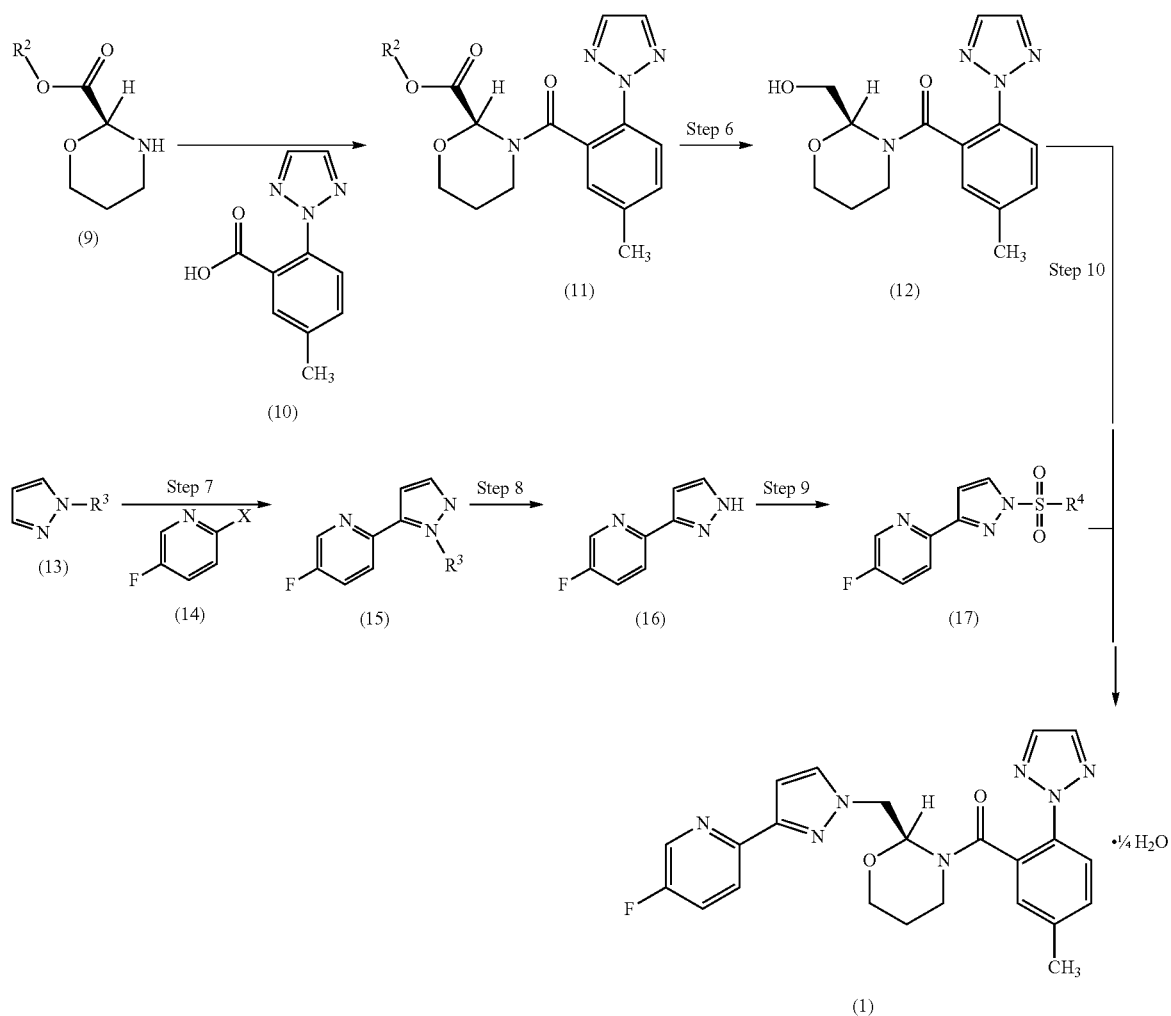

(In the above formulas, $R^1$, $R^2$, $R^3$, $R^4$ and X have the same meanings as defined hereinabove.)

Step 1: A compound of formula (2) is reacted with glyoxylic acid in a polar solvent in the presence of abase to thereby prepare a compound of formula (3). Then, after a polar solvent and abase are further added, the compound of formula (3) is reacted with a compound of formula (4) to obtain a compound of formula (5).

As the polar solvent, use can be made of the following, for example, at both times of synthesis of the compounds of formulas (3) and (5): an alcoholic solvent such as methanol, ethanol or isopropanol; tetrahydrofuran; acetonitrile; water; or a mixed solvent thereof.

As the base, use can be made of the following, for example, at both times of synthesis of the compounds of formulas (3) and (5): an inorganic base such as sodium hydroxide, potassium hydroxide, lithium hydroxide, sodium phosphate, potassium phosphate, sodium carbonate, potassium carbonate, sodium bicarbonate, or potassium bicarbonate.

The reaction temperature adopted at both times of synthesis of the compounds of formulas (3) and (5) can be generally in the range of −20° C. to the boiling point of a solvent used, preferably in the range of −15 to 60° C., more preferably in the range of −10 to 10° C.

The amount of the base used upon synthesis of the compound of formula (3) can be in the range of 0.5 to 5 molar equivalents, preferably in the range of 1 to 3 molar equivalents, more preferably in the range of 1 to 1.5 molar equivalents, relative to the compound of formula (2) as a source material. That amount upon synthesis of the compound of formula (5) can be in the range of 0.5 to 5 molar equivalents, preferably in the range of 1 to 3 molar equivalents, more preferably in the range of 1.3 to 2.0 molar equivalents, relative to the compound of formula (2) as a source material.

The amount of glyoxylic acid used can be in the range of 0.5 to 5 molar equivalents, preferably in the range of 1 to 3 molar equivalents, more preferably in the range of 1 to 1.5 molar equivalents, relative to the compound of formula (2) as a source material.

The amount of the compound of formula (4) used can be in the range of 0.5 to 5 molar equivalents, preferably in the range of 1 to 3 molar equivalents, more preferably in the range of 1 to 2.5 molar equivalents, relative to the compound of formula (2) as a source material.

The amount of the solvent used upon synthesis of the compound of formula (3) can be in the range of 1 to 100 times by mass, preferably in the range of 1 to 30 times by mass, more preferably in the range of 1 to 20 times by mass, relative to the compound of formula (2) as a source material. That amount upon synthesis of the compound of formula (5) can be in the range of 1 to 100 times by mass, preferably in the range of 1 to 50 times by mass, more preferably in the range of 1 to 30 times by mass, relative to the compound of formula (2) as a source material.

The compound of formula (5) can be obtained as a product refined by chromatography, recrystallization, re-slurry, crystallization or other similar method, or as an unrefined product.

Step 2: The compound of formula (5) is stirred in an inert solvent under dropwise addition of a chiral amine to thereby obtain a compound of formula (6).

As the inert solvent, use can be made of the following, for example: an ester solvent such as ethyl acetate or isopropyl acetate; an alcoholic solvent such as methanol, ethanol or isopropanol; an ether-based solvent such as tetrahydrofuran, 2-methyltetrahydrofuran, tetrahydropyran, diethyl ether, diisopropyl ether, tert-butyl methyl ether, cyclopentyl methyl ether, 1,2-dimethoxyethane, diethoxymethane or 1,4-dioxane; or acetonitrile; or a mixed solvent thereof.

As the chiral amine, use can be made of a compound having an asymmetric center at the α-position of the amino group, such as (R)-phenylethylamine, (R)-1-(p-tolyl)ethyl-amine, (R)-1-(4-methoxyphenyl)-ethylamine, (R)-1-(4-chlorophenyl)-ethylamine, (S)-3,3-dimethyl-2-butylamine, (1S,2R)-2-amino-1-phenyl-1,3-propanediol, L-phenylalani-nol, (R)-phenylglycinol, (R)-2-amino-1-propanol, or cin-chonidine.

The reaction temperature can be generally in the range of −20° C. to the boiling point of a solvent used, preferably in the range of −15 to 15° C., more preferably in the range of −10 to 10° C.

The equivalent amount of the chiral amine used can be in the range of 0.2 to 2 molar equivalents, preferably in the range of 0.45 to 0.65 molar equivalents, more preferably in the range of 0.50 to 0.60 molar equivalents, relative to the compound of formula (5).

The amount of the solvent used can be in the range of 1 to 100 times by mass, preferably in the range of 1 to 30 times by mass, more preferably in the range of 5 to 10 times by mass, relative to the compound of formula (5).

The compound of formula (6) can be obtained as a product refined by recrystallization, re-slurry, neutralizing crystallization or other similar method.

Step 3: The compound of formula (6) is reacted with an acid in a mixed solvent of water and an inert solvent to thereby obtain a compound of formula (7).

As the inert solvent, use can be made of the following, for example: an alcoholic solvent such as methanol, ethanol or 2-propanol; a hydrocarbon-based solvent such as toluene or xylene; a halogenated solvent such as chloroform, 1,2-dichloroethane, carbon tetrachloride, chlorobenzene, 1,2-dichlorobenzene or benzotrifluoride; an ether-based solvent such as tetrahydrofuran, 2-methyltetrahydrofuran, tetrahydropyran, diethyl ether, diisopropyl ether, tert-butyl methyl ether, cyclopentyl methyl ether, 1,2-dimethoxyethane, diethoxymethane or 1,4-dioxane; acetonitrile; dimethyl sulfoxide; or a mixed solvent thereof.

As the acid, hydrochloric acid, sulfuric acid, phosphoric acid, acetic acid or the like can be used.

The reaction temperature can be generally in the range of −10° C. to the boiling point of a solvent used, preferably in the range of −5 to 50° C., more preferably in the range of 0 to 40° C.

The amount of the acid used can be in the range of 0.5 to 5 molar equivalents, preferably in the range of 1 to 3 molar equivalents, more preferably in the range of 1 to 2 molar equivalents, relative to the compound of formula (6) as a source material.

The amount of the solvent used can be in the range of 1 to 100 times by mass, preferably in the range of 1 to 30 times by mass, more preferably in the range of 5 to 15 times by mass, relative to the compound of formula (6) as a source material.

The compound of formula (7) can be obtained as a product refined by chromatography, recrystallization, re-slurry, neutralizing crystallization or other similar method, or as an unrefined product.

Step 4: The compound of formula (7) is reacted with $R^2OH$ in an inert solvent in the presence of an acid to thereby obtain a compound of formula (8) according to the present invention.

As the inert solvent, use can be made of the following, for example: a hydrocarbon-based solvent such as toluene, xylene, benzene, heptane, hexane, cyclohexane or petroleum ether; a halogenated solvent such as dichloromethane, chloroform, 1,2-dichloroethane, carbon tetrachloride, chlorobenzene or benzotrifluoride; an ether-based solvent such as tetrahydrofuran, 2-methyltetrahydrofuran, tetrahydropyran, diethyl ether, diisopropyl ether, tert-butyl methyl ether, cyclopentyl methyl ether or 1,4-dioxane; acetonitrile; or a mixed solvent thereof.

As the acid, use can be made of hydrochloric acid, sulfuric acid, phosphoric acid, acetic acid, trifluoroacetic acid, p-toluenesulfonic acid, trifluoromethanesulfonic acid, methanesulfonic acid, or an acid chloride (e.g., thionyl chloride, oxalyl chloride) that can react with $R^2OH$ to produce an acid.

The substituent $R^2$ in $R^2OH$ has the same meaning as defined hereinabove. As the $R^2OH$ group, use can be made of methanol, ethanol, propanol, isopropanol, butanol, isobutyl alcohol, tert-butyl alcohol, allyl alcohol, benzyl alcohol, or the like.

The reaction temperature can be generally in the range of −20° C. to the boiling point of a solvent used, preferably in the range of −5 to 40° C., more preferably in the range of 10 to 30° C.

The amount of the acid used can be in the range of 0.1 to 5 molar equivalents, preferably in the range of 1 to 4 molar equivalents, more preferably in the range of 1 to 2 molar equivalents, relative to the compound of formula (7).

The amount of $R^2OH$ used can be in the range of 0.1 to 100 times by mass, preferably in the range of 1 to 30 times by mass, more preferably in the range of 1 to 10 times by mass, relative to the compound of formula (7).

The amount of the solvent used can be in the range of 0 to 100 times by mass, preferably in the range of 0 to 30 times by mass, more preferably in the range of 1 to 10 times by mass, relative to the compound of formula (7).

The compound of formula (8) can be obtained as a product refined by chromatography, recrystallization, re-slurry, neutralizing crystallization or other similar method, or as an unrefined product.

Step 5: In this step, the amino group at the 1-position of the compound of formula (8) is deprotected to prepare a compound of formula (9), which is then reacted with a compound of formula (10) to obtain a compound of formula (11).

For the deprotection reaction in this step, any appropriate deprotection conditions can be selected and used depending on the properties of a protective group. For example, when $R^1$ is a benzyloxy group, the compound of formula (8) is allowed to react using a palladium-on-carbon catalyst and hydrogen gas in an inert solvent in the presence of a base, whereby a compound of formula (9) is prepared. Then, the compound of formula (9) is condensed with an acid chloride of formula (10) to obtain a compound of formula (11). The acid chloride of formula (10) can be prepared by reacting the compound of formula (10) with an acid chloride in an inert solvent.

As the inert solvent, use can be made of the following, for example, upon preparation of the compound of formula (9): a hydrocarbon-based solvent such as toluene, xylene, benzene, heptane, hexane or petroleum ether; a halogenated solvent such as dichloromethane, chloroform, 1,2-dichloroethane, carbon tetrachloride, chlorobenzene or benzotrifluoride; an ether-based solvent such as tetrahydrofuran, 2-methyltetrahydrofuran or tetrahydropyran; an ester solvent such as ethyl acetate or isopropyl acetate; or a mixed solvent thereof. Upon preparation of the acid chloride of formula (10), use can be made of the following, for example: a hydrocarbon-based solvent such as toluene, xylene, benzene or heptane; an ether-based solvent such as tetrahydrofuran, 2-methyltetrahydrofuran or tetrahydropyran; or a mixed solvent thereof. Upon synthesis of the compound of formula (11), use can be made of the following, for example: a hydrocarbon-based solvent such as toluene, xylene, benzene or heptane; a halogenated solvent such as dichloromethane, chloroform, 1,2-dichloroethane, carbon tetrachloride, chlorobenzene or benzotrifluoride; an ether-based solvent such as tetrahydrofuran, 2-methyltetrahydrofuran or tetrahydropyran; an ester solvent such as ethyl acetate or isopropyl acetate; or a mixed solvent thereof.

The reaction temperature adopted upon preparation of the compound of formula (9) can be generally in the range of −20° C. to the boiling point of a solvent used, preferably in the range of −5 to 50° C., more preferably in the range of 0 to 40° C.

That temperature upon preparation of the acid chloride of formula (10) can be generally in the range of 0° C. to the boiling point of a solvent used, preferably in the range of 10 to 70° C., more preferably in the range of 30 to 60° C. That temperature upon synthesis of the compound of formula (11) can be generally in the range of 0° C. to the boiling point of a solvent used, preferably in the range of 0 to 50° C., more preferably in the range of 0 to 30° C.

As the base, triethylamine, diisopropylamine, pyridine, 2,4,6-tetramethylpyridine or the like can be used.

The amount of the base used can be in the range of 0 to 5 molar equivalents, preferably in the range of 1 to 4 molar equivalents, more preferably in the range of 1 to 3 molar equivalents, relative to the compound of formula (8) as a source material.

The amount of palladium-on-carbon used can be in the range of 0.001 to 1 molar equivalents, preferably in the range of 0.005 to 0.5 molar equivalents, more preferably in the range of 0.01 to 0.4 molar equivalents, relative to the compound of formula (8) as a source material.

The amount of the compound of formula (10) used can be in the range of 0.7 to 3 molar equivalents, preferably in the range of 0.8 to 2 molar equivalents, more preferably in the range of 0.9 to 1.5 molar equivalents, relative to the compound of formula (8) as a source material.

As the acid chloride used for conversion into the acid chloride of formula (10), use can be made of thionyl chloride, phosphorus trichloride, phosphorus pentachloride, oxalyl chloride, or the like.

The amount of the acid chloride used can be in the range of 0.5 to 5 molar equivalents, preferably in the range of 1 to 2 molar equivalents, more preferably in the range of 1 to 1.5 molar equivalents, relative to the compound of formula (10) as a source material.

The amount of the solvent used upon preparation of the compound of formula (9) can be in the range of 1 to 100 times by mass, preferably in the range of 1 to 30 times by mass, more preferably in the range of 1 to 10 times by mass, relative to the compound of formula (7). That amount upon preparation of the acid chloride of formula (10) can be in the range of 1 to 100 times by mass, preferably in the range of 1 to 30 times by mass, more preferably in the range of 1 to 10 times by mass, relative to the compound of formula (10).

The compound of formula (11) can be obtained as a product refined by chromatography, recrystallization, re-slurry, crystallization or other similar method, or as an unrefined product.

Step 6: The compound of formula (11) is reacted with a reducing agent in an alcoholic solvent and an ether-based solvent to thereby obtain a compound of formula (12).

As the alcoholic solvent, use can be made of, for example, methanol, ethanol, propanol, isopropanol, or a mixed solvent thereof. As the ether-based solvent, used can be made of tetrahydrofuran, 2-methyltetrahydrofuran, tetrahydropyran, diethyl ether, diisopropyl ether, tert-butyl methyl ether, cyclopentyl methyl ether, 1,2-dimethoxyethane, diethoxymethane, 1,4-dioxane, or the like.

As the reducing agent, use can be made of the following, for example: sodium borohydride, lithium borohydride, lithium aluminum hydride, lithium triethylborohydride, sodium bis(2-methoxyethoxy)aluminum hydride, lithium tri (sec-butyl)borohydride, potassium tri(sec-butyl)borohydride, diisobutylaluminum hydride, borane-tetrahydrofuran complex, borane-dimethylsulfide complex, or the like.

The reaction temperature can be generally in the range of −20° C. to the boiling point of a solvent used, preferably in the range of −5 to 40° C., more preferably in the range of 0 to 20° C.

The amount of the reducing agent used can be in the range of 0.5 to 8 molar equivalents, preferably in the range of 2 to 6 molar equivalents, more preferably in the range of 3 to 5 molar equivalents, relative to the compound of formula (11).

The amount of the solvent used can be in the range of 1 to 100 times by mass, preferably in the range of 1 to 30 times by mass, more preferably in the range of 1 to 10 times by mass, relative to the compound of formula (11).

The compound of formula (12) can be obtained as a product refined by chromatography, recrystallization, re-slurry, neutralizing crystallization or other similar method, or as an unrefined product.

Step 7: A base and a zinc reagent are added to a compound of formula (13) in an inert solvent to prepare an arylzinc reagent, which is then allowed to undergo a Negishi reaction with a compound of formula (14) using a catalyst, whereby a compound of formula (15) can be obtained.

As the inert solvent used for preparation of an arylzinc reagent, use can be made of the following, for example: a hydrocarbon-based solvent such as toluene, xylene, benzene, heptane, hexane or cyclohexane; an ester solvent such as ethyl acetate or isopropyl acetate; an ether-based solvent such as tetrahydrofuran, 2-methyltetrahydrofuran, tetrahydropyran, diethyl ether, diisopropyl ether, tert-butyl methyl ether, cyclopentyl methyl ether, 1,2-dimethoxyethane, diethoxymethane or 1,4-dioxane; or a mixed solvent thereof.

As the inert solvent used for preparation of a zinc reagent during a Negishi reaction, use can be made of the following, for example: a hydrocarbon-based solvent such as toluene, xylene, benzene, heptane, hexane or cyclohexane; an ester solvent such as ethyl acetate or isopropyl acetate; an ether-based solvent such as tetrahydrofuran, 2-methyltetrahydrofuran, tetrahydropyran, diethyl ether, diisopropyl ether, tert-butyl methyl ether, cyclopentyl methyl ether, 1,2-dimethoxyethane, diethoxymethane or 1,4-dioxane; an amide-based solvent such as N,N-dimethylformamide, N,N-dimethylacetoxyamide or N-methyl-2-pyrrolidone; or a mixed solvent thereof.

As the base, use can be made of the following, for example: n-butyllithium, n-hexyllithium, sodium bis(trimethylsilyl)amide, potassium bis(trimethylsilyl)amide, or the like.

As the zinc reagent, for example, zinc chloride, zinc bromide, or the like can be used.

As the catalyst, use can be made of the following, for example: a palladium catalyst such as palladium chloride, palladium acetate, bis(triphenylphosphine)palladium dichloride, or tetrakis(triphenylphosphine)palladium; or a nickel catalyst such as bis(triphenylphosphine)nickel dichloride. If necessary, a phosphine ligand such as triphenylphosphine or tris(2-methylphenyl)phosphine may be added in addition to the catalyst mentioned above.

The temperature of preparation of an arylzinc reagent can be generally in the range of −78° C. to the boiling point of a solvent used, preferably in the range of −78 to 30° C., more preferably in the range of −20 to 10° C. The reaction temperature for a Negishi reaction can be generally in the range of 0° C. to the boiling point of a solvent used, preferably in the range of 20 to 100° C., more preferably in the range of 40 to 70° C.

The amount of the base used can be in the range of 0.1 to 5 molar equivalents, preferably in the range of 0.2 to 3 molar equivalents, more preferably in the range of 1 to 2 molar equivalents, relative to the compound of formula (14).

The amount of the zinc reagent used can be in the range of 0.1 to 5 molar equivalents, preferably in the range of 0.2 to 3 molar equivalents, more preferably in the range of 1 to 2 molar equivalents, relative to the compound of formula (14).

The amount of the catalyst used can be in the range of 0.001 to 1.0 molar equivalents, preferably in the range of 0.001 to 0.1 molar equivalents, more preferably in the range of 0.01 to 0.04 molar equivalents, relative to the compound of formula (14). In a preferred mode, a phosphine ligand can be added and used in an amount of 0.001 to 1.0 molar equivalents, preferably 0.001 to 0.1 molar equivalents, more preferably 0.01 to 0.04 molar equivalents, relative to the compound of formula (14).

The amount of the solvent used can be in the range of 1 to 100 times by mass, preferably in the range of 1 to 30 times by mass, more preferably in the range of 1 to 20 times by mass, relative to the compound of formula (13).

The compound of formula (15) can be obtained as a product refined by chromatography, recrystallization, re-slurry, neutralizing crystallization or other similar method, or as an unrefined product.

Step 8: For the deprotection reaction in this step, any appropriate deprotection conditions can be selected and used depending on the properties of a protective group. To be specific, when $R^3$ is an oxan-2-yl group (tetrahydropyranyl (THP) group), the compound of formula (15) is generally reacted with an acid in an inert solvent to obtain a compound of formula (16). Any other type of solvent may be used instead of the inert solvent.

As the acid, use can be made of the following, for example: a Brønsted acid such as hydrochloric acid, sulfuric acid, methanesulfonic acid or trifluoroacetic acid; or a Lewis acid such as boron trifluoride-diethyl ether complex or aluminum chloride.

As the inert solvent, use can be made of the following, for example: a halogenated solvent such as dichloromethane, chloroform, 1,2-dichloroethane or chlorobenzene; a hydrocarbon-based solvent such as toluene, xylene, benzene, heptane, hexane or cyclohexane; an ester solvent such as ethyl acetate or isopropyl acetate; an ether-based solvent such as tetrahydrofuran, 2-methyltetrahydrofuran, tetrahydropyran, diethyl ether, diisopropyl ether, tert-butyl methyl ether, cyclopentyl methyl ether, 1,2-dimethoxyethane, diethoxymethane or 1,4-dioxane; an amide-based solvent such as N,N-dimethylformamide, N,N-dimethylacetoxyamide or N-methyl-2-pyrrolidone; or a mixed solvent thereof. Also, water, or an alcohol such as methanol, ethanol or propanol, may be used as a solvent. One or more of the above solvents may be used in combination with an inert solvent.

The reaction temperature can be generally in the range of −80° C. to the boiling point of a solvent used, preferably in the range of 0 to 100° C., more preferably in the range of 15 to 30° C.

The amount of the acid used can be in the range of 0.01 to 20 molar equivalents, preferably in the range of 0.1 to 10 molar equivalents, more preferably in the range of 0.1 to 5 molar equivalents, relative to the compound of formula (15) as a source material.

The amount of the solvent used can be in the range of 1 to 100 times by mass, preferably in the range of 1 to 30 times by mass, more preferably in the range of 1 to 10 times by mass, relative to the compound of formula (2) as a source material.

The compound of formula (16) can be obtained as a product refined by chromatography, recrystallization, re-slurry, neutralizing crystallization or other similar method, or as an unrefined product.

Step 9: The compound of formula (16) is reacted with $R^4SO_2$—X or $(R^4SO_2)_2O$ in a basic solvent to obtain a compound of formula (17).

As the basic solvent, use can be made of, for example, triethylamine, diisopropylamine, pyridine, 2,4,6-tetramethylpyridine, or the like.

The substituents $R^4$ and X in $R^4SO_2$—X or $(R^4SO_2)_2O$ have the same meanings as defined hereinabove, and for example, methanesulfonyl chloride, methanesulfonic anhydride, p-toluenesulfonyl chloride, p-toluenesulfonic anhydride, trifluoromethanesulfonyl chloride, trifluoromethanesulfonic anhydride, or the like can be used.

The reaction temperature can be generally in the range of −20° C. to the boiling point of a solvent used, preferably in the range of −5 to 40° C., more preferably in the range of 0 to 30° C.

The amount of $R^4SO_2$—X or $(R^4SO_2)_2O$ used can be in the range of 0.5 to 7 molar equivalents, preferably in the range of 1 to 5 molar equivalents, more preferably in the range of 1 to 3 molar equivalents, relative to the compound of formula (16).

The amount of the solvent used can be in the range of 1 to 100 times by mass, preferably in the range of 1 to 30 times by mass, more preferably in the range of 1 to 10 times by mass, relative to the compound of formula (16).

The compound of formula (17) can be obtained as a product refined by chromatography, recrystallization, re-slurry, crystallization or other similar method, or as an unrefined product.

Step 10: The compound of formula (12) is reacted with the compound of formula (17) in an inert solvent in the presence of a base to thereby yield the compound of formula (1).

As the inert solvent, use can be made of the following, for example: a hydrocarbon-based solvent such as toluene, xylene, benzene or heptane; an ether-based solvent such as tetrahydrofuran, 2-methyltetrahydrofuran or tetrahydropyran; acetonitrile; pyridine; 2,4,6-tetramethylpyridine; or a mixed solvent thereof.

As the base, for example, sodium bis(trimethylsilyl)amide, potassium bis(trimethylsilyl)amide, n-butyllithium, n-hexyllithium, or the like can be used.

The reaction temperature can be generally in the range of −20° C. to the boiling point of a solvent used, preferably in the range of −5 to 80° C., more preferably in the range of 0 to 70° C.

The amount of the compound of formula (17) used can be in the range of 0.5 to 7 molar equivalents, preferably in the range of 1 to 5 molar equivalents, more preferably in the range of 1 to 3 molar equivalents, relative to the compound of formula (12).

The amount of the base used can be in the range of 0.5 to 7 molar equivalents, preferably in the range of 1 to 5 molar equivalents, more preferably in the range of 1 to 3 molar equivalents, relative to the compound of formula (12).

The amount of the solvent used can be in the range of 1 to 100 times by mass, preferably in the range of 1 to 30 times by mass, more preferably in the range of 1 to 10 times by mass, relative to the compound of formula (12).

The compound of formula (1) can be obtained as a product refined by chromatography, recrystallization, re-slurry, crystallization or other similar method, or as an unrefined product.

[Chemical Formula 28]

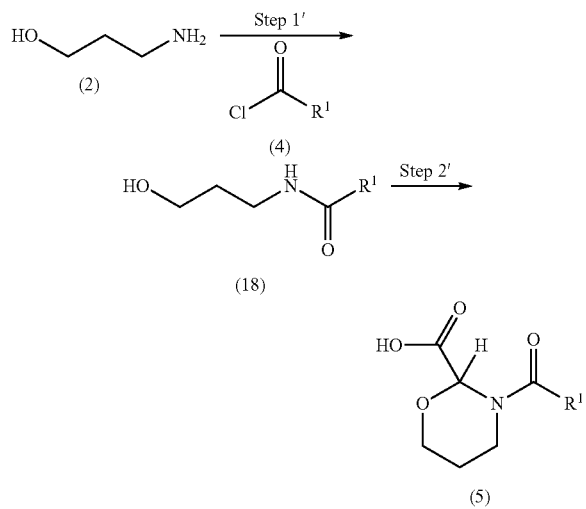

(In the above formulas, $R^1$ has the same meaning as defined hereinabove.)

Step 1': A compound of formula (2) is reacted with a compound of formula (4)-m a polar solvent in the presence of a base to thereby obtain a compound of formula (18).

As the polar solvent, use can be made of the following, for example: an alcoholic solvent such as methanol, ethanol or isopropanol; tetrahydrofuran; acetonitrile; water; or a mixed solvent thereof.

As the base, use can be made of, for example, an inorganic base such as sodium hydroxide, potassium hydroxide, lithium hydroxide, sodium phosphate, potassium phosphate, sodium carbonate, potassium carbonate, sodium bicarbonate, or potassium bicarbonate.

The reaction temperature can be generally in the range of −20° C. to the boiling point of a solvent used, preferably in the range of −10 to 60° C., more preferably in the range of 0 to 30° C.

The amount of the base used can be in the range of 0.5 to 7 molar equivalents, preferably in the range of 1 to 6 molar equivalents, more preferably in the range of 1 to 5 molar equivalents, relative to the compound of formula (2).

The amount of the compound of formula (4) used can be in the range of 0.5 to 5 molar equivalents, preferably in the range of 1 to 4 molar equivalents, more preferably in the range of 1 to 3 molar equivalents, relative to the compound of formula (2).

The amount of the solvent used can be in the range of 1 to 100 times by mass, preferably in the range of 1 to 30 times by mass, more preferably in the range of 1 to 20 times by mass, relative to the compound of formula (2).

The compound of formula (18) can be obtained as a product refined by chromatography, recrystallization, re-slurry, crystallization or other similar method, or as an unrefined product.

Step 2': The compound of formula (18) is reacted with glyoxylic acid in an acidic solvent to thereby obtain a compound formula (5).

As the acidic solvent, for example, acetic acid, trifluoroacetic acid, hydrochloric acid, sulfuric acid or the like can be used.

The reaction temperature can be generally in the range of −20° C. to the boiling point of a solvent used, preferably in the range of 0 to 70° C., more preferably in the range of 20 to 60° C.

The amount of glyoxylic acid used can be in the range of 0.5 to 5 molar equivalents, preferably in the range of 1 to 4 molar equivalents, more preferably in the range of 1 to 3 molar equivalents, relative to the compound of formula (18) as a source material.

The amount of the solvent used can be in the range of 1 to 100 times by mass, preferably in the range of 1 to 30 times by mass, more preferably in the range of 1 to 20 times by mass, relative to the compound of formula (2).

The compound of formula (5) can be obtained as a product refined by chromatography, recrystallization, re-slurry, crystallization or other similar method, or as an unrefined product.

[Chemical Formula 29]

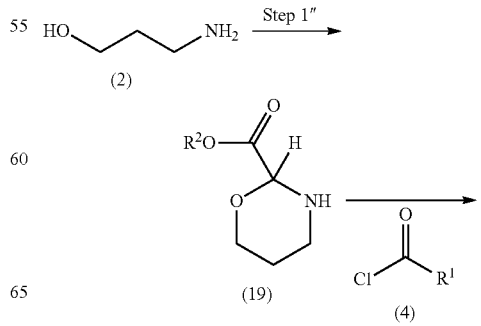

-continued $R^2O$—[structure with CHO, O, N-R¹, ring] (20) →Step 2″→ HO—[structure with CHO, O, N-R¹, ring] (5)

(In the above formulas, $R^1$ and $R^2$ have the same meanings as defined above.)

Step 1″: A compound of formula (2) is reacted with a glyoxylic acid ester in an inert solvent to synthesize a compound of formula (19). Then, after an inert solvent and a base are further added, the compound of formula (19) is reacted with a compound of formula (4) to thereby obtain a compound of formula (20).

As the inert solvent, use can be made of the following, for example, at both times of synthesis of the compounds of formulas (19) and (20): a hydrocarbon-based solvent such as toluene, xylene, benzene or heptane; a halogenated solvent such as chloroform, 1,2-dichloroethane, carbon tetrachloride, chlorobenzene, 1,2-dichlorobenzene or benzotrifluoride; an ether-based solvent such as tetrahydrofuran, 2-methyltetrahydrofuran, tetrahydropyran, diethyl ether, diisopropyl ether, tert-butyl methyl ether, cyclopentyl methyl ether, 1,2-dimethoxyethane, diethoxymethane or 1,4-dioxane; acetonitrile; or a mixed solvent thereof.

As the base, for example, triethylamine, diisopropylamine, pyridine, 2,4,6-tetramethylpyridine or the like can be used.

As the glyoxylic acid ester, use can be made of an alkyl or aralkyl ester of glyoxylic acid, such as methyl glyoxylate, ethyl glyoxylate, propyl glyoxylate, isopropyl glyoxylate, n-butyl glyoxylate, tert-butyl glyoxylate, allyl glyoxylate, hexyl glyoxylate, benzyl glyoxylate or menthyl glyoxylate.

The reaction temperature adopted at both times of synthesis of the compounds of formulas (19) and (20) can be generally in the range of −20° C. to the boiling point of a solvent used, preferably in the range of −10 to 70° C., more preferably in the range of 0 to 60° C.

The amount of the glyoxylic acid ester used can be in the range of 0.5 to 5 molar equivalents, preferably in the range of 1 to 3 molar equivalents, more preferably in the range of 1 to 1.5 molar equivalents, relative to the compound of formula (2).

The amount of the base used can be in the range of 0.5 to 5 molar equivalents, preferably in the range of 1 to 4 molar equivalents, more preferably in the range of 1 to 3 molar equivalents, relative to the compound of formula (2).

The amount of the compound of formula (4) used can be in the range of 0.5 to 5 molar equivalents, preferably in the range of 1 to 4 molar equivalents, more preferably in the range of 1 to 3 molar equivalents, relative to the compound of formula (2).

The amount of the solvent used at both times of synthesis of the compounds of formulas (19) and (20) can be in the range of 1 to 100 times by mass, preferably in the range of 1 to 30 times by mass, more preferably in the range of 1 to 20 times by mass, relative to the compound of formula (2).

The compound of formula (20) can be obtained as a product refined by chromatography, recrystallization, re-slurry, crystallization or other similar method, or as an unrefined product.

Step 2″: The compound of formula (20) is reacted with a base and water in an inert solvent to thereby yield a compound of formula (5).

As the inert solvent, use can be made of the following: an alcoholic solvent such as methanol, ethanol or isopropanol; a hydrocarbon-based solvent such as toluene, xylene, benzene or heptane; a halogenated solvent such as chloroform, 1,2-dichloroethane, carbon tetrachloride, chlorobenzene, 1,2-dichlorobenzene or benzotrifluoride; an ether-based solvent such as tetrahydrofuran, 2-methyltetrahydrofuran, tetrahydropyran, diethyl ether, diisopropyl ether, tert-butyl methyl ether, cyclopentyl methyl ether, 1,2-dimethoxyethane, diethoxymethane or 1,4-dioxane; acetonitrile; or a mixed solvent thereof.

As the base, use can be made of, for example, an inorganic base such as sodium hydroxide, potassium hydroxide or lithium hydroxide.

The reaction temperature can be generally in the range of −20° C. to the boiling point of a solvent used, preferably in the range of −10 to 70° C., more preferably in the range of 0 to 40° C.

The amount of the base used can be in the range of 0.5 to 7 molar equivalents, preferably in the range of 1 to 6 molar equivalents, more preferably in the range of 1 to 5 molar equivalents, relative to the compound of formula (20) as a source material.

The amount of the solvent used can be in the range of 1 to 100 times by mass, preferably in the range of 1 to 30 times by mass, more preferably in the range of 1 to 20 times by mass, relative to the compound of formula (20).

The compound of formula (5) can be obtained as a product refined by chromatography, recrystallization, re-slurry, crystallization or other similar method, or as an unrefined product.

EXAMPLES

Hereunder, the present invention will be specifically described in more detail by way of working examples. However, this invention should not be interpreted to be limited to the examples provided below. Some of the yields achieved in the working examples provided below were affected by the reaction conditions. Higher yields can be achieved by selecting optimized reaction conditions.

The instrumental analytical data mentioned in the Examples section were measured by the following measurement instruments.
Mass spectroscopy (MS): LCMS-IT-TOF (Shimadzu); ionization: ESI/APCI
CHN elemental analysis: vario MICRO cube (Elementar)
Ton chromatography analysis: XS-100 (Mitsubishi Chemical)
Infrared spectroscopic analysis (IR): Spectrum One (Perkin Elmer)
High-performance liquid chromatography analysis (HPLC): Prominence (Shimadzu)
The abbreviations used herein are listed below.
MS: mass spectrometry
ESI: electrospray ionization
APCI: atmospheric pressure chemical ionization
wt. %: percent concentration by weight
Some of the compounds may be named using nomenclature software like ACD/Name Version 2015 (Advanced Chemistry Development Inc.).

Hereunder, the present invention will be described in more detail by way of working and comparative examples, but this invention is not limited to these examples.

Example 1

Synthesis of (2S)-3-[(benzyloxy)carbonyl]-1,3-oxazinane-2-carboxylic acid-(2R)-2-amino-2-phenylethan-1-ol (1/1) (25)

[Chemical Formula 30]

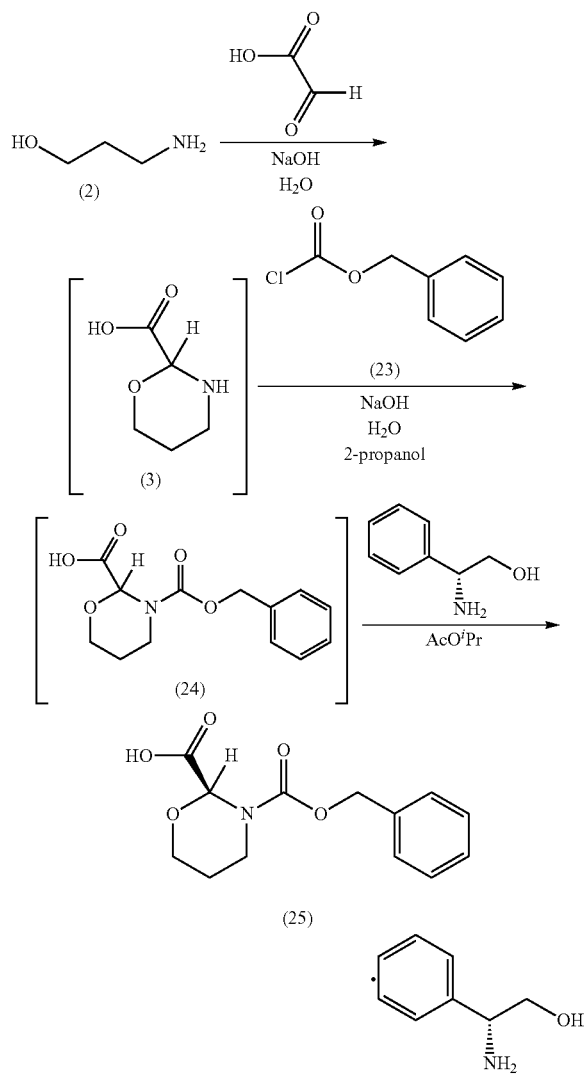

A 50% glyoxylic acid aqueous solution (108.43 g) was added dropwise to an aqueous solution (250.09 g) of sodium hydroxide (29.30 g) at not more than 10° C., and washing was done with water (50.00 g). Next, a solution of 3-aminopropan-1-ol (2) (50.00 g) in water (50.00 g) was added dropwise at not more than 10° C., washing was done with water (50.00 g), and stirring was continued at not more than 10° C. overnight. Then, 2-propanol (350 g) was added dropwise, and the reaction solution was cooled to −10° C. and adjusted to pH 10.0 with a 50% sodium hydroxide aqueous solution. Next, a solution of benzyl chloroformate (23) (136.27 g) in 2-propanol (500.00 g) was added dropwise such that the inner temperature was maintained at not more than 0° C. Further, in this process, a 50% sodium hydroxide aqueous solution was further added dropwise, as appropriate, such that the pH of the reaction solution fell within the range of 9.5 to 10.5. After dropwise addition, washing was done with 2-propanol (50.00 g). After completion of dropwise addition, stirring was continued at −10° C. for 4 hours. 712.42 g of the reaction solution was subjected to distillation under reduced pressure, methyl tert-butyl ether (254.15 g) was added, and the reaction solution was phase separated. Next, concentrated hydrochloric acid was added to the aqueous phase at not more than 10° C. to adjust the pH to 2.12, isopropyl acetate (250.47 g) and common salt (50.00 g) were added, and the reaction solution was phase separated. Again, the aqueous phase was phase separated with isopropyl acetate (250.27 g), and the first and second isopropyl acetate phases were mixed.

Isopropyl acetate was added to adjust the total amount to 1550.02 g, and concentration was done to give a total amount of 516.49 g. Again, isopropyl acetate was added to adjust the total amount to 1584.06 g, and the temperature was raised to 60° C. (2R)-2-amino-2-phenylethan-1-ol (23.27 g) was added with stirring, and the stirring was continued for 8 hours. Then, (2R)-2-amino-2-phenylethan-1-ol (23.27 g) was added, and the mixture was cooled to −10° C., stirred at that temperature overnight, and subjected to filtration and washing with isopropyl acetate (500.00 g) three times, whereby (2S)-3-[(benzyloxy)carbonyl]-1,3-oxazinane-2-carboxylic acid-(2R)-2-amino-2-phenylethan-1-ol 1/1 (25) (99.22 g, 99.17% ee) was obtained.

MS (ESI/APCI Dual) m/z: 266 [(M+H)$^+$], 288 [(M+Na)$^+$], 264 [(M−H)$^-$]. IR (KBr) cm$^{-1}$: 3437, 2883, 1679, 1646, 1595, 1535, 1432, 1389, 1344, 1274, 1219, 1141, 1077, 1031, 752, 701. Anal. Calcd for $C_{21}H_{26}N_2O_6$: C, 62.67; H, 6.51; N, 6.96. Found: C, 62.71; H, 6.48; N, 6.98. The HPLC retention time for (25) was about 14.5 min. The HPLC analysis was done under the following conditions: column: YMC Triart C18 (3.0 mmφ×100 mm, 3 μm); column temperature: 40° C.; flow rate: 0.7 mL/min.; detection wavelength: 230 nm (UV); mobile phase: solution A: 0.1% v/v phosphoric acid aqueous solution, solution B: methanol:acetonitrile=3:1 (v/v); and gradient conditions: changed from 90:10 A:B to 10:90 A:B over 20 min., held at 10:90 A:B for 5 min., reverted back to 90:10 A:B over 0.1 min., and held at 90:10 A:B for 9.9 min.

Example 2

Synthesis of methyl (2S)-3-[5-methyl-2-(2H-1,2,3-triazol-2-yl)benzoyl]-1,3-oxazinane-2-carboxylate (30)

[Chemical Formula 31]

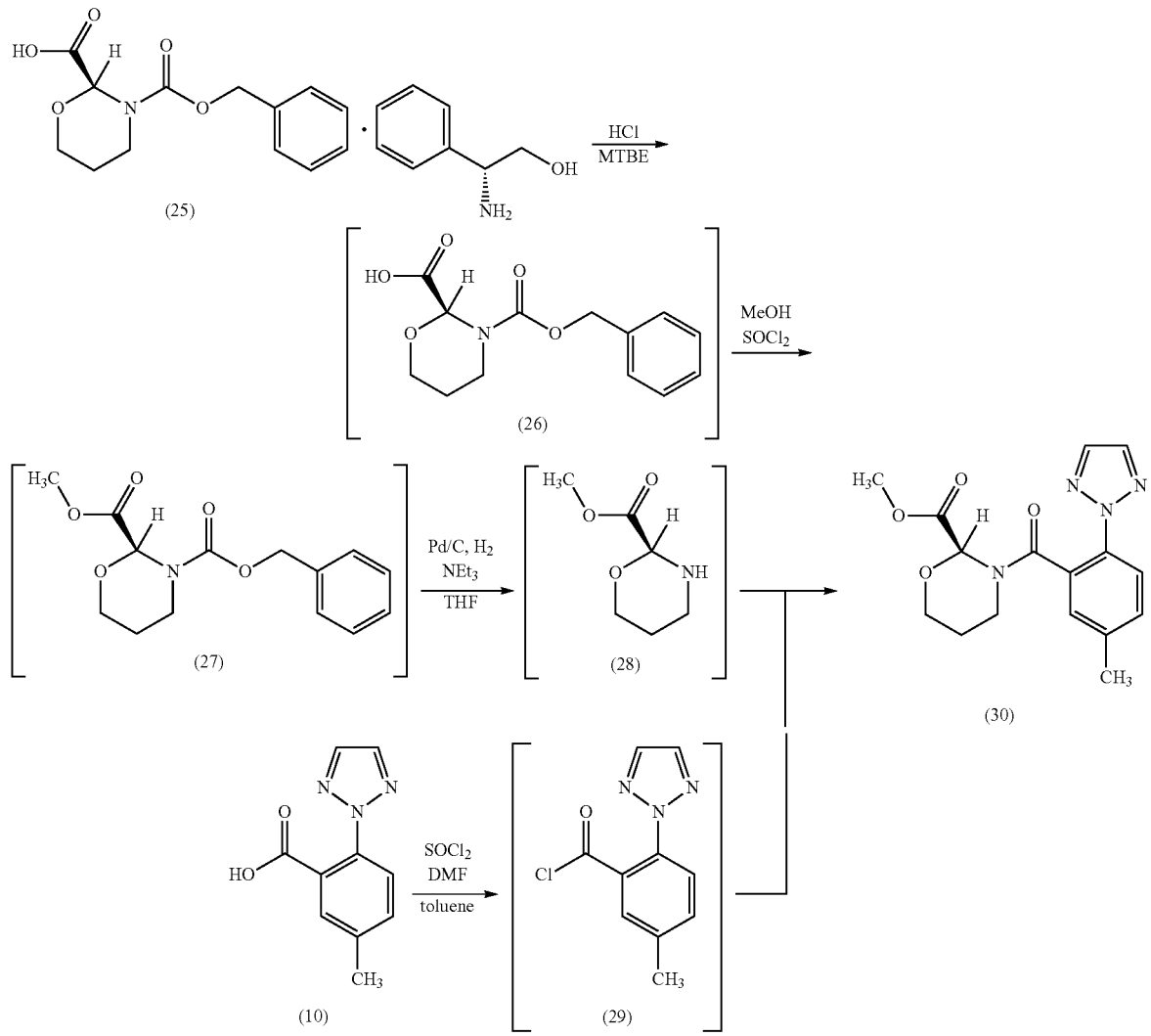

To (2S)-3-[(benzyloxy)carbonyl]-1,3-oxazinane-2-carboxylic acid-(2R)-2-amino-2-phenylethan-1-ol (1/1) (25) (15.00 g), methyl tert-butyl ether (75.42 g) was added followed by 10% hydrochloric acid (20.45 g), and stirring was done for 0.5 hour. After still standing followed by removal of the aqueous phase, methanol (75.00 g) was added, and thionyl chloride (5.33 g) was added dropwise under ice-cooling, and stirring was continued for 14 hours. After completion of the reaction, the reaction solution was neutralized with 2 mol/L sodium hydroxide under ice-cooling. Then, ethyl acetate (106.63 g) was added, and the solution was concentrated to a total amount of 91.48 g. Again, ethyl acetate (105.19 g) was added and the aqueous phase was removed; thereafter, the organic phase was concentrated to 23.22 g and tetrahydrofuran (75.01 g) was added. This process of concentration and addition of tetrahydrofuran was repeated to make the solution into a tetrahydrofuran solution. Next, a 5% palladium-on-carbon catalyst (4.69 g) and triethylamine (7.83 g) were added, and stirring was continued for 4 hours in a hydrogen atmosphere. The reaction mixture was filtered through cellulose powder and washed with tetrahydrofuran (31.42 g) to obtain a tetrahydrofuran solution A. Separately, dimethylformamide (0.02 g) and thionyl chloride (3.75 g) were added to a toluene (31.56 g) solution of 5-methyl-2-(2H-1,2,3-triazol-2-yl)benzoic acid (6.28 g), and stirring was done at 56° C. for 1.5 hours. Then, the reaction solution was concentrated to a total amount of 9.20 g to obtain a toluene solution A. The toluene solution A was added dropwise to the tetrahydrofuran solution A under ice-cooling, followed by washing with toluene (9.65 g) and stirring at room temperature for 12 hours. Then, after washing with a 10% sodium bicarbonate aqueous solution (31.42 g), the aqueous phase was extracted with toluene (31.42 g) and washed with 10% brine (31.42 g). After the solution was concentrated to a total amount of 18.86 g, toluene (20.72 g) was added, and the solution was concentrated again to a total amount of 18.88 g. Further, toluene (20.73 g) was added, and the solution was concentrated yet again to a total amount of 12.58 g, and then, toluene was added to give a total amount of 44.00 g. Heptane (20.85 g) was added, and the solution was stirred at 65° C. and cooled to 44° C., followed by dropwise addition of heptane (49.01 g). After cooling with ice, the mixture was stirred for 11 hours, filtrated, and washed with heptane (43.98 g), whereby methyl (2S)-3-[5-methyl-2-(2H-1,2,3-triazol-2-yl)benzoyl]-1,3-oxazinane-2-carboxylate (30) (9.69 g) was obtained.

MS (ESI/APCI Dual) m/z: 331 [(M+H)+], 353 [(M+Na)+]. IR (KBr) cm−1: 2967, 1745, 1662, 1407, 1090, 1009. The HPLC retention time for (30) was about 15.3 min. [HPLC retention time for (26): about 14.5 min.] [HPLC retention time for (27): about 16.7 min.]. The HPLC analysis was done under the following conditions: column: YMC Triart C18 (3.0 mmφ×100 mm, 3 μm); column temperature: 40° C.; flow rate: 0.7 mL/min.; detection wavelength: 230 nm (UV); mobile phase: solution A: 0.1% v/v phosphoric acid aqueous solution, solution B: methanol:acetonitrile=3:1 (v/v); and gradient conditions: changed from 90:10 A:B to 10:90 A:B over 20 min., held at 10:90 A:B for 5 min., reverted back to 90:10 A:B over 0.1 min., and held at 90:10 A:B for 9.9 min.

(26): MS (ESI/APCI Dual) m/z: 266 [(M+H)+], 288 [(M+Na)+], 264 [(M−H)−].

(27): MS (ESI/APCI Dual) m/z: 280 [(M+H)+], 302 [(M+Na)+].

Example 3

Synthesis of [(2S)-2-(hydroxymethyl)-1,3-oxazinan-3-yl][5-methyl-2-(2H-1,2,3-triazol-2-yl)phenyl]methanone (12)

[Chemical Formula 32]

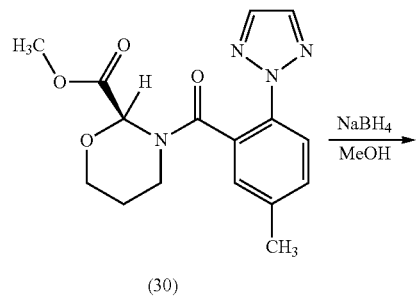

To the solution of methyl (2S)-3-[5-methyl-2-(2H-1,2,3-triazol-2-yl)benzoyl]-1,3-oxazinane-2-carboxylate (30) (30.00 g) in methanol (240.00 g), sodium borohydride (6.872 g) was added under water cooling, and stirring was done for 2 hours. Further, sodium borohydride (6.872 g) was added and stirring was done for 2.5 hours. After adjusted to pH 4 with 2 mol/L hydrochloric acid and stirred overnight, the reaction solution was adjusted to pH 7 with 2 mol/L sodium hydroxide aqueous solution and concentrated to a total amount of 246.42 g. 2-methyltetrahydrofuran (450.03 g) was added, and the solution was phase separated and washed with 2 mol/L sodium hydroxide (151.58 g) having common salt (15.05 g) dissolved therein and with 20% brine (151.43 g). In the process of washing with 20% brine, the aqueous phase was adjusted to pH 7 with 2 mol/L hydrochloric acid. Next, the solution was concentrated to a total amount of 90.01 g, and stirring was done at 40° C. After cooling to −10° C., followed by addition of heptane (60.00 g) and stirring for 6 hours, the filtered solid was washed with a 2-methyltetrahydrofuran/heptane (1:9 v/v) mixed solution (60.01 g), whereby [(2S)-2-(hydroxymethyl)-1,3-oxazinan-3-yl][5-methyl-2-(2H-1,2,3-triazol-2-yl)phenyl]methanone (12) (24.94 g) was obtained.

MS (ESI/APCI Dual) m/z: 303 [(M+H)+], 325 [(M+Na)+]. IR (KBr) cm−1: 3467, 1649, 1637, 1416, 1058. Anal. Calcd for $C_{15}H_{15}N_4O_3$: C, 59.59; H, 6.00; N, 18.53. Found: C, 59.60; H, 5.97; N, 18.65. The HPLC retention time for (12) was about 12.9 min. The HPLC analysis was done under the following conditions: column: YMC Triart C18 (3.0 mmφ×100 mm, 3 μm); column temperature: 40° C.; flow rate: 0.7 mL/min.; detection wavelength: 230 nm (UV); mobile phase: solution A: 0.1% v/v phosphoric acid aqueous solution, solution B: methanol:acetonitrile=3:1 (v/v); and gradient conditions: changed from 90:10 A:B to 10:90 A:B over 20 min., held at 10:90 A:B for 5 min., reverted back to 90:10 A:B over 0.1 min., and held at 90:10 A:B for 9.9 min.

Example 4

Synthesis of 5-fluoro-2-(1H-pyrazol-3-yl)pyridine (16)

[Chemical Formula 33]

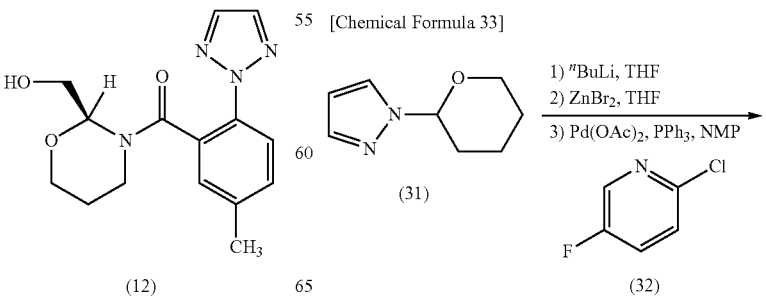

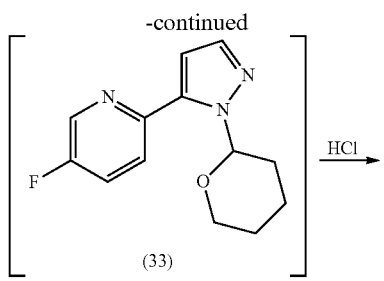

A of 1-(oxan-2-yl)-1H-pyrazole (31) (23.2 g) in tetrahydrofuran (121 g) was cooled to 5° C. in a nitrogen atmosphere, and then a n-hexane solution (100 mL) of 1.6 mol/L n-butyllithium was added dropwise, and the mixture was stirred for 50 minutes to prepare a slurry A.

The slurry A was added to a solution of zinc bromide (37.3 g) in tetrahydrofuran (83.8 g) at a temperature below 30° C. in a nitrogen atmosphere. After washing with tetrahydrofuran (6.16 g) and stirring for 1 hour, the resulting two-phase solution (upper phase A and lower phase A) was settled and stored for 17 hours.

Next, 2-chloro-5-fluoropyridine (32) (13.4 g) was dissolved in N-methyl-2-pyrrolidone (124 g) in a nitrogen atmosphere, and triphenylphosphine (0.537 g) and palladium acetate (0.231 g) were added, followed by heating at 61° C. The lower phase A of the settled solution was added dropwise over 2 hours, followed by washing with N-methyl-2-pyrrolidone (13.8 g). After stirring for 5 hours, the solution was cooled to 10° C., and a 20 wt. % ammonium chloride aqueous solution (135 g) and toluene (58.9 g) were added. After filtration through a pad of cellulose powder (13.7 g), the pad was washed with toluene (12.0 g). The combined filtrate was phase separated, and the aqueous phase was extracted with toluene (58.1 g). The combined organic phases were washed twice with 10 wt. % brine (67.4 g, 67.0 g). Then, NH-silica gel (13.6 g) was added, and the mixture was stirred for 1 hour followed by filtration. After washed with methanol (32.3 g), the filtrate was concentrated to obtain a concentrate (34.4 g).

To the obtained concentrate, methanol (53.1 g) and concentrated hydrochloric acid (2.24 g) were added, and the mixture was stirred for 2 hours. After addition of 15 mol/L sodium hydroxide aqueous solution (3.74 g) and water (108 g), the mixture was concentrated to obtain a concentrate (107 g). Next, concentrated hydrochloric acid (13.0 g) and toluene (29.4 g) were added, and the solution was phase separated. To the resulting aqueous phase, a 15 mol/L sodium hydroxide aqueous solution (9.75 g) was added dropwise to adjust the pH to 2.3. After stirring for 17.5 hours, filtration was done and the cake was washed with water (41.0 g). The obtained wet crystal was vacuum dried at a setting of 50° C. to thereby obtain 5-fluoro-2-(1H-pyrazol-3-yl)pyridine (16) (12.8 g).

MS (ESI/APCI Dual) m/z: 164 [(M+H)$^+$], 186 [(M+Na)$^+$]. IR (KBr) cm$^{-1}$: 3201, 1491, 1232, 1104, 927. The HPLC retention time for (16) was about 4.6 min. [HPLC retention time for (33): about 11.4 min.]. The HPLC analysis was done under the following conditions: column: YMC Triart C18 (4.6 mmφ×150 mm, 5 μm); column temperature: 40° C.; flow rate: 1.0 mL/min.; detection wavelength: 230 nm (UV); mobile phase: solution A: 0.1% v/v phosphoric acid aqueous solution, solution B: acetonitrile; gradient conditions: held at 74:26 A:B for 1 min., changed to 29:71 A:B over 10 min., held at 29:71 A:B for 2 min., reverted back to 74:26 A:B over 0.1 min., and held at 74:26 A:B for 4.9 min.

Example 5

Synthesis of 5-fluoro-2-[1-(methanesulfonyl)-1H-pyrazol-3-yl]pyridine (34)

[Chemical Formula 34]

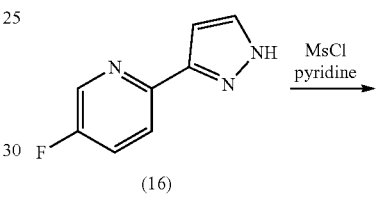

To 5-fluoro-2-(1H-pyrazol-3-yl)pyridine (16) (5.00 g), pyridine (17 mL) was added, and methanesulfonyl chloride (3.690 g) was further added at 1° C. After the solution was stirred at room temperature for 7 hours followed by cooling, water (30 mL) was added at not more than 15° C., and stirring was continued at not more than 5° C. for 2 hours. The reaction mixture was filtrated and washed with water (15 mL) to thereby obtain 5-fluoro-2-[1-(methanesulfonyl)-1H-pyrazol-3-yl]pyridine (34) (6.51 g).

MS (ESI/APCI Dual) m/z: 242 [(M+H)$^+$]. IR (KBr) cm$^{-1}$: 3000, 1378, 1184, 1153, 1037, 772, 557. Anal. Calcd for $C_9H_8FN_3O_2S$: C, 44.81; H, 3.34; N, 17.42. Found: C, 44.79; H, 3.37; N, 17.46. The HPLC retention time for (34) was about 13.0 min. The HPLC analysis was done under the following conditions: column: YMC Triart C18 (3.0 mmφ×100 mm, 3 μm); column temperature: 40° C.; flow rate: 0.7 mL/min.; detection wavelength: 230 nm (UV); mobile phase: solution A: 0.1% v/v phosphoric acid aqueous solution, solution B: methanol:acetonitrile=3:1 (v/v); and gradient conditions: changed from 90:10 A:B to 10:90 A:B over 20 min., held at 10:90 A:B for 5 min., reverted back to 90:10 A:B over 0.1 min., and held at 90:10 A:B for 9.9 min.

Example 6

Synthesis of a (2S)-(2-{[3-(5-fluoropyridin-2-yl)-1H-pyrazol-1-yl]methyl}-1,3-oxazinan-3-yl)[5-methyl-2-(2H-1,2,3-triazol-2-yl)phenyl]methanone hydrate (1)

[Chemical Formula 35]

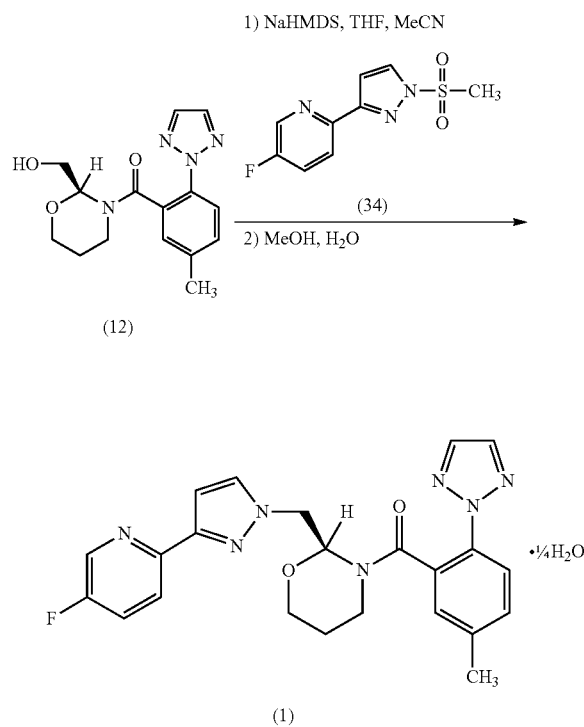

To the solution of [(2S)-2-(hydroxymethyl)-1,3-oxazinan-3-yl][5-methyl-2-(2H-1,2,3-triazol-2-yl)phenyl]methanone (12) (5.00 g) in tetrahydrofuran (25 mL), 5-fluoro-2-[1-(methanesulfonyl)-1H-pyrazol-3-yl]pyridine (34) (4.79 g) and acetonitrile (10 mL) were added, and the mixture was cooled to 1° C. Then, sodium bis(trimethylsilyl)amide (39.8% solution in tetrahydrofuran, 10.0 mL) was added, and stirring was done for 1 hour. Next, acetonitrile (7.5 mL) was added, and the mixture was heated to 64° C. and stirred for 2.5 hours. After cooling to room temperature, water (10 mL) was added, and the reaction solution was phase separated followed by filtration to remove foreign objects and washing with methanol (10.01 g). After the solution was vacuum concentrated to 20.88 g, methanol (25.00 g) was added, and the solution was vacuum concentrated again to 17.80 g. Again, methanol (27.20 g) was added, and the solution was vacuum concentrated to 25.33 g. Then, methanol was added to adjust the total amount to 42.00 g. After the temperature was raised to 60° C. and water (6.00 g) was added, the solution was cooled to 0° C. followed by further addition of water (30.03 g) and stirring at 0° C. overnight. The mixture was filtered and washed with a cool methanol:water mixed solution (3:2 v/v, 14.00 g) to thereby obtain a (2S)-(2-{[3-(5-fluoropyridin-2-yl)-1H-pyrazol-1-yl]methyl}-1,3-oxazinan-3-yl)[5-methyl-2-(2H-1,2,3-triazol-2-yl)phenyl]methanone hydrate (1) (6.45 g).

MS (ESI/APCI Dual) m/z: 448 [(M+H)$^+$], 470 [(M+Na)$^+$], 446 [(M−H)$^−$]. IR (KBr) cm$^{-1}$: 3453, 1629, 1505, 1457, 1445, 1431, 1407, 1226, 1077, 1005, 783. Anal. Calcd for $C_{23}H_{22.5}FN_7O_{2.25}$: C, 61.12; H, 5.02; N, 21.69. Found: C, 61.08; H, 4.96; N, 21.76. The HPLC retention time for (1) was about 17.9 min. The HPLC analysis was done under the following conditions: column: YMC Triart C18 (3.0 mmφ× 100 mm, 3 μm); column temperature: 40° C.; flow rate: 0.7 mL/min.; detection wavelength: 230 nm (UV); mobile phase: solution A: 0.1% v/v phosphoric acid aqueous solution, solution B: methanol:acetonitrile=3:1 (v/v); and gradient conditions: changed from 90:10 A:B to 10:90 A:B over 20 min., held at 10:90 A:B for 5 min., reverted back to 90:10 A:B over 0.1 min., and held at 90:10 A:B for 9.9 min.

Example 7

Synthesis of benzyl(3-hydroxypropyl)carbamate (35)

[Chemical Formula 36]

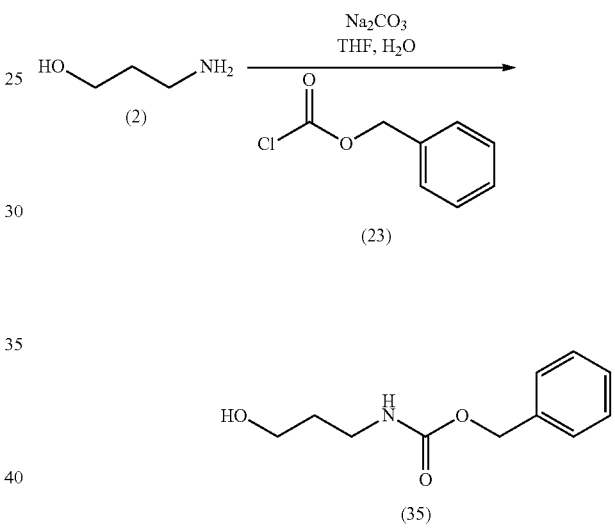

To a solution of sodium carbonate (26.50 g) in water (150.22 g), 3-aminopropan-1-ol (2) (15.22 g) was added at room temperature, and then a solution of benzyl chloroformate (23) (37.53 g) in tetrahydrofuran (60.09 g) was added at not more than 10° C., followed by stirring at room temperature overnight. After the pH was adjusted to 7.0 with concentrated hydrochloric acid at not more than 10° C., tetrahydrofuran was distilled off by vacuum concentration, methyl tert-butyl ether (150.12 g) was added, and the solution was phase separated. Next, ethyl acetate (60.01 g) and sodium sulfate (15.01 g) were added, followed by stirring, filtration, washing with ethyl acetate (30.03 g), and concentration. After crystallization with methyl tert-butyl ether (150.01 g) and heptane (37.51 g), the product was filtrated and washed with a mixed solvent of methyl tert-butyl ether (25.00 g) and heptane (5.00 g) to thereby obtain benzyl(3-hydroxypropyl)carbamate (35) (35.26 g).

MS (ESI/APCI Dual) m/z: 210 [(M+H)$^+$], 232 [(M+Na)$^+$]. IR (KBr) cm$^{-1}$: 3326, 1684, 1534, 1262, 697. Anal. Calcd for $C_{11}H_{15}NO_3$: C, 63.14; H, 7.23; N, 6.69. Found: C, 63.02; H, 7.18; N, 6.64. The HPLC retention time for (35) was about 12.2 min. The HPLC analysis was done under the following conditions: column: YMC Triart C18 (3.0 mmφ× 100 mm, 3 μm); column temperature: 40° C.; flow rate: 0.7 mL/min.; detection wavelength: 230 nm (UV); mobile phase: solution A: 0.1% v/v phosphoric acid aqueous solution, solution B: methanol:acetonitrile=3:1 (v/v); and gradient conditions: changed from 90:10 A:B to 10:90 A:B over 20 min., held at 10:90 A:B for 5 min., reverted back to 90:10 A:B over 0.1 min., and held at 90:10 A:B for 9.9 min.

Example 8

Synthesis of 3-[(benzyloxy)carbonyl]-1,3-oxazinane-2-carboxylic acid (24)

[Chemical Formula 37]

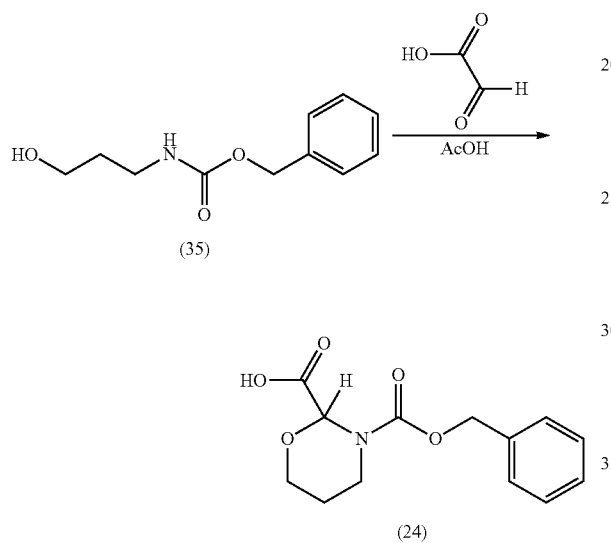

To a 50% glyoxylic acid aqueous solution (2.960 g), acetic acid (7.41 g) and compound (35) (4.18 g) were added, and stirring was continued at 60° C. for 17 hours. After the solution was concentrated, a 1 mol/L NaOH aqueous solution (70 mL) and methyl tert-butyl ether (50 mL) were added, and the solution was phase separated. Then, concentrated hydrochloric acid was added to the aqueous phase at not more than 10° C. to adjust the pH to 2.00, and the solution was phase separated with ethyl acetate (50 mL). Column purification was done with chloroform and methanol, whereby 3-[(benzyloxy)carbonyl]-1,3-oxazinane-2-carboxylic acid (24) (2.78 g) was obtained.

MS (ESI/APCI Dual) m/z: 266 [(M+H)$^+$], 288 [(M+Na)$^+$], 264 [(M−H)$^−$]. IR (KBr) cm$^{−1}$: 2960, 1751, 1636, 1458, 1450, 1147, 1091, 968. Anal. Calcd for $C_{13}H_{15}NO_5$: C, 58.86; H, 5.70; N, 5.28. Found: C, 58.83; H, 5.73; N, 5.32. The HPLC retention time for (24) was about 14.5 min. The HPLC analysis was done under the following conditions: column: YMC Triart C18 (3.0 mmφ×100 mm, 3 μm); column temperature: 40° C.; flow rate: 0.7 mL/min.; detection wavelength: 230 nm (UV); mobile phase: solution A: 0.1% v/v phosphoric acid aqueous solution, solution B: methanol:acetonitrile=3:1 (v/v); and gradient conditions: changed from 90:10 A:B to 10:90 A:B over 20 min., held at 10:90 A:B for 5 min., reverted back to 90:10 A:B over 0.1 min., and held at 90:10 A:B for 9.9 min.

Example 9

Synthesis of 3-[(benzyloxy)carbonyl]-1,3-oxazinane-2-carboxylic acid (24)

[Chemical Formula 38]

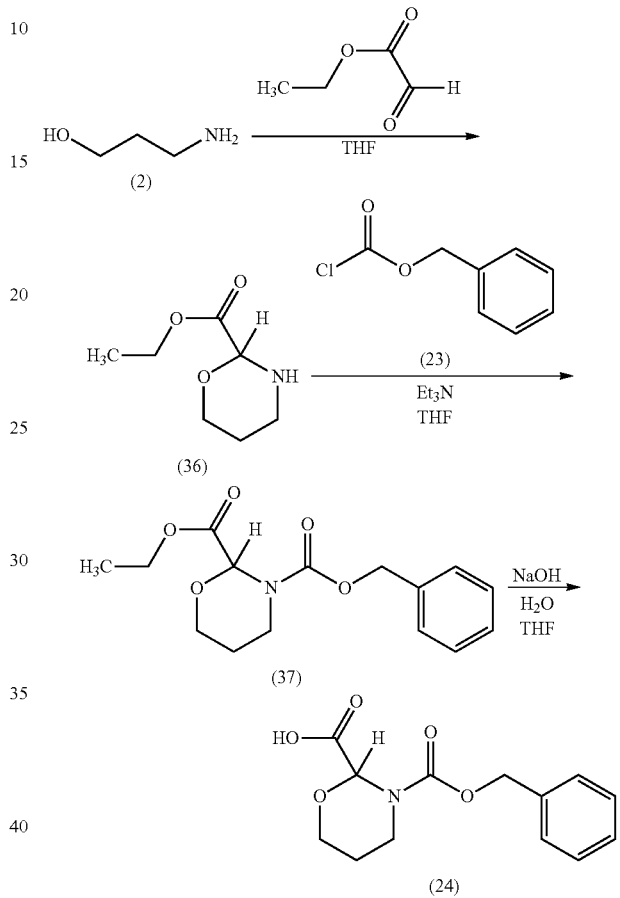

To a solution of ethyl glyoxylate in toluene (47%, 16.10 g), tetrahydrofuran (55.00 g) and a solution of 3-aminopropan-1-ol (2) (5.20 g) in tetrahydrofuran (5.01 g) were added, and stirring was continued at 51° C. for 3 hours. After the solution was concentrated, tetrahydrofuran (26.00 g) and triethylamine (15.41 g) were added, and then benzyl chloroformate (23) (12.99 g) was added at 4° C. After the mixture was stirred at room temperature for 2 hours, a 10% sodium hydroxide aqueous solution (55.00 g) was added at not more than 10° C., and stirring was continued at room temperature overnight. Next, tetrahydrofuran was distilled off by concentration, and the solution was adjusted to pH 1.23 with concentrated hydrochloric acid, extracted with chloroform (25 mL) four times, and the organic solution was washed with water (10 mL). Sodium sulfate (10.00 g) was added, followed by stirring, filtration, washing with chloroform (25 mL), and concentration. Thereafter, tetrahydrofuran (25.00 g), a 10% sodium hydroxide aqueous solution (25.00 g), and methanol (10.00 g) were added, and stirring was continued at room temperature for 1 hour. After the solution was washed with chloroform (25 mL) twice, the aqueous phase was adjusted to pH 1.21 with concentrated hydrochloric acid, extracted with chloroform (25 mL) four times, and the combined organic solution was washed with water (10 mL). Sodium sulfate (10.01 g) was added, followed by stirring, filtration, washing with chloroform (10 mL), and concentration. The concentrate was purified by silica gel chromatography to thereby obtain 3-[(benzyloxy) carbonyl]-1,3-oxazinane-2-carboxylic acid (24) (8.120 g).

The spectral data of (24) were consistent with those obtained in Example 8.

INDUSTRIAL APPLICABILITY

The present invention allows for inexpensive and easy scale-up of a production process for a (2S)-(2-{[3-(5-fluoropyridin-2-yl)-1H-pyrazol-1-yl]methyl}-1,3-oxazinan-3-yl)[5-methyl-2-(2H-1,2,3-triazol-2-yl)phenyl]methanone hydrate represented by formula (1), and enables provision of a production process suitable for mass production of said compound.

The invention claimed is:
1. A process for producing (2S)-(2-{[3-(5-fluoropyridin-2-yl)-1H-pyrazol-1-yl]methyl}-1,3-oxazinan-3-yl)[5-methyl-2-(2H-1,2,3-triazol-2-yl)phenyl]methanone hydrate represented by formula (1):

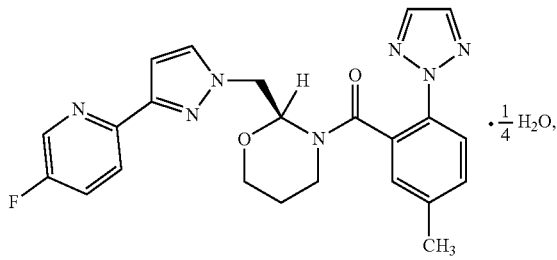

(1)

comprising
(a) reacting a compound represented by formula (2):

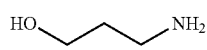

(2)

with glyoxylic acid to convert them into a compound represented by formula (3):

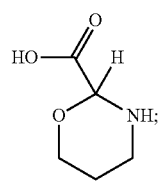

(3)

(b) condensing the compound represented by formula (3) with a compound represented by formula (4):

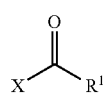

(4)

wherein $R^1$ represents a hydrogen atom, an optionally substituted $C_{1-6}$ alkyl group, an optionally substituted $C_{2-6}$ alkenyl group, a optionally substituted $C_{2-6}$ alkynyl group, an optionally substituted $C_{3-6}$ cycloalkyl group, an optionally substituted $C_{3-6}$ cycloalkenyl group, an optionally substituted $C_{1-6}$ alkoxy group, an optionally substituted $C_{2-6}$ alkenyloxy group, an optionally substituted $C_{2-6}$ alkynyloxy group, an optionally substituted $C_{3-6}$ cycloalkoxy group, an optionally substituted $C_{3-6}$ cycloalkenyloxy group, an optionally substituted aryl group, an optionally substituted heteroaryl group, a saturated or partially saturated heterocyclyl group which is optionally substituted, or an optionally substituted $C_{7-12}$ aralkyloxy group, and X represents a halogen atom, to convert them into a compound represented by formula (5):

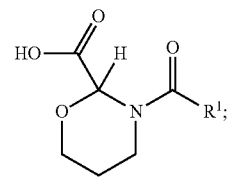

(5)

(c) converting the compound represented by formula (5) into a compound represented by formula (6):

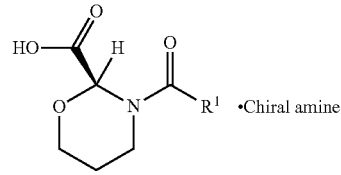

(6)

wherein "chiral amine" represents an optically active amine capable of forming a salt with carboxylic acid;
(d) converting the compound represented by formula (6) into a compound represented by formula (7):

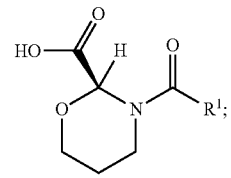

(7)

(e) converting the compound represented by formula (7) into a compound represented by formula (8):

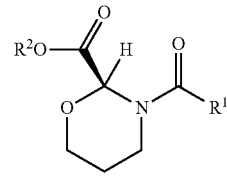

(8)

wherein R² represents a protective group for carboxylic acid;

(f) converting the compound represented by formula (8) into a compound represented by formula (9):

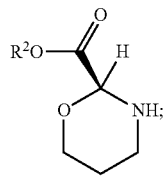

(9)

(g) condensing the compound represented by formula (9) with a compound represented by formula (10):

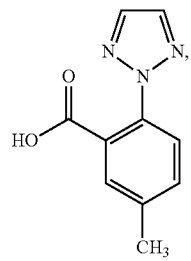

(10)

to convert them into a compound represented by formula (11):

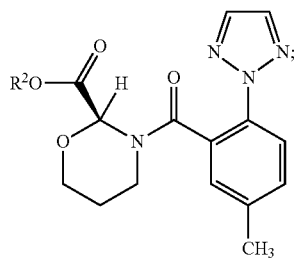

(11)

(h) converting the compound represented by formula (11) into a compound represented by formula (12):

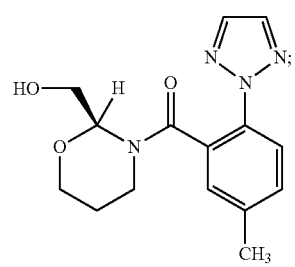

(12)

(i) reacting a compound represented by formula (13):

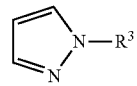

(13)

wherein R³ represents a protective group for pyrazole, with a compound represented by formula (14):

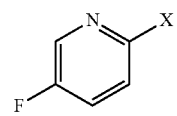

(14)

to convert them into a compound represented by formula (15):

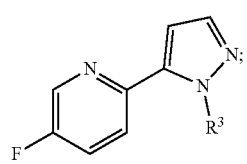

(15)

(j) converting the compound represented by formula (15) into a compound represented by formula (16):

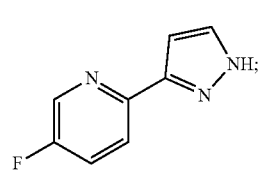

(16)

(k) reacting the compound represented by formula (16) with R⁴SO₂—X or (R⁴SO₂)₂O to convert them into a compound represented by formula (17):

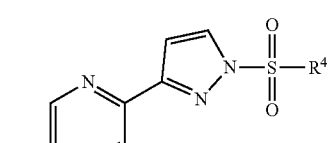

(17)

wherein R⁴ represents an optionally substituted alkyl group, or an optionally substituted aryl group; and (l) reacting the compound represented by formula (12) with the compound represented by formula (17) to convert them into the compound represented by formula (1).

2. A process for producing a compound represented by formula (5):

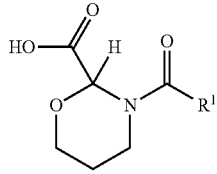
(5)

wherein R¹ represents a hydrogen atom, an optionally substituted $C_{1-6}$ alkyl group, an optionally substituted $C_{2-6}$ alkenyl group, a optionally substituted $C_{2-6}$ alkynyl group, an optionally substituted $C_{3-6}$ cycloalkyl group, an optionally substituted $C_{3-6}$ cycloalkenyl group, an optionally substituted $C_{1-6}$ alkoxy group, an optionally substituted $C_{2-6}$ alkenyloxy group, an optionally substituted $C_{2-6}$ alkynyloxy group, an optionally substituted $C_{3-6}$ cycloalkoxy group, an optionally substituted $C_{3-6}$ cycloalkenyloxy group, an optionally substituted aryl group, an optionally substituted heteroaryl group, a saturated or partially saturated heterocyclyl group which is optionally substituted, or an optionally substituted $C_{7-12}$ aralkyloxy group, comprising:

(a) condensing the compound represented by formula (2)

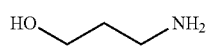
(2)

with the compound represented by formula (4)

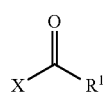
(4)

wherein X represents a halogen atom, to convert them into a compound represented by formula (18):

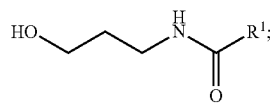
(18)

and (b) reacting the compound represented by formula (18) with glyoxylic acid to convert them into the compound represented by formula (5).

3. A process for producing a compound represented by formula (5):

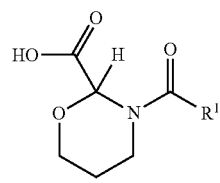
(5)

wherein R¹ represents a hydrogen atom, an optionally substituted $C_{1-6}$ alkyl group, an optionally substituted $C_{2-6}$ alkenyl group, a optionally substituted $C_{2-6}$ alkynyl group, an optionally substituted $C_{3-6}$ cycloalkyl group, an optionally substituted $C_{3-6}$ cycloalkenyl group, an optionally substituted $C_{1-6}$ alkoxy group, an optionally substituted $C_{2-6}$ alkenyloxy group, an optionally substituted $C_{2-6}$ alkynyloxy group, an optionally substituted $C_{3-6}$ cycloalkoxy group, an optionally substituted $C_{3-6}$ cycloalkenyloxy group, an optionally substituted aryl group, an optionally substituted heteroaryl group, a saturated or partially saturated heterocyclyl group which is optionally substituted, or an optionally substituted $C_{7-12}$ aralkyloxy group, comprising:

(a) reacting the compound represented by formula (2)

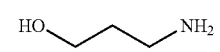
(2)

with a glyoxylic acid ester to convert them into a compound represented by formula (19):

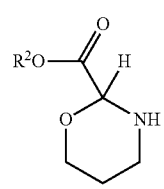
(19)

wherein R² represents a protective group for carboxylic acid;

(b) condensing the compound represented by formula (19) with the compound represented by formula (4)

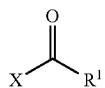
(4)

wherein X represents a halogen atom, to convert them into a compound represented by formula (20):

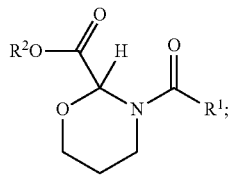
(20)

and (c) converting the compound represented by formula (20) into the compound represented by formula (5).

4. A compound represented by formula (21):

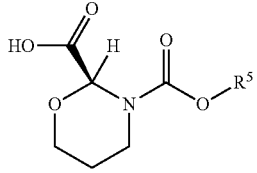
(21)

wherein R⁵ represents an optionally substituted $C_{7\text{-}12}$ aralkyl group; or an enantiomer thereof, or a salt thereof.

5. A compound represented by formula (22):

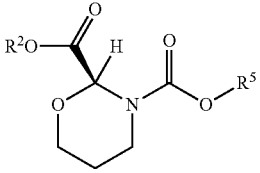
(22)

wherein R² represents a protective group for carboxylic acid and R⁵ represents an optionally substituted $C_{7\text{-}12}$ aralkyl group; or an enantiomer thereof.

* * * * *